US009464069B2

(12) United States Patent
Torrens-Jover et al.

(10) Patent No.: US 9,464,069 B2
(45) Date of Patent: Oct. 11, 2016

(54) 1,2-DISUBSTITUTED CYCLOBUTYL COMPOUNDS

(71) Applicant: LABORATORIOS DEL DR. ESTEVE S.A., Barcelona (ES)

(72) Inventors: Antoni Torrens-Jover, Terrassa (ES); Rosa Ortuño-Mingarro, Barcelona (ES); Àlex Pericas-Cano, Canovelles (ES); Èric Ferrer-Mallofrè, Rubi (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/907,899

(22) PCT Filed: Jul. 29, 2014

(86) PCT No.: PCT/EP2014/066223
§ 371 (c)(1),
(2) Date: Jan. 27, 2016

(87) PCT Pub. No.: WO2015/014816
PCT Pub. Date: Feb. 5, 2015

(65) Prior Publication Data
US 2016/0185755 A1    Jun. 30, 2016

(30) Foreign Application Priority Data

Jul. 30, 2013  (EP) .................................. 13382310

(51) Int. Cl.
| | | |
|---|---|---|
| C07C 211/17 | (2006.01) |
| C07D 401/12 | (2006.01) |
| C07D 207/06 | (2006.01) |
| C07D 295/03 | (2006.01) |
| C07D 211/14 | (2006.01) |
| C07D 231/22 | (2006.01) |

(52) U.S. Cl.
CPC ........... *C07D 401/12* (2013.01); *C07C 211/17* (2013.01); *C07D 207/06* (2013.01); *C07D 211/14* (2013.01); *C07D 231/22* (2013.01); *C07D 295/03* (2013.01)

(58) Field of Classification Search
CPC  C07D 401/12; C07D 207/06; C07D 295/03; C07D 211/14; C07D 231/22; C07D 211/17; C07C 211/17
See application file for complete search history.

(56) References Cited

FOREIGN PATENT DOCUMENTS

| | | | |
|---|---|---|---|
| ES | WO 2008015266 A1 * | 2/2008 | ........... C07C 69/675 |
| WO | WO2006021463 | 3/2006 | |
| WO | WO2007098961 | 9/2007 | |
| WO | WO2007121976 | 11/2007 | |
| WO | WO2008015266 | 2/2008 | |
| WO | WO2008055932 | 5/2008 | |
| WO | WO2008055933 | 5/2008 | |
| WO | WO2009071657 | 6/2009 | |

OTHER PUBLICATIONS

Bowen, Wayne, D., "Sigma receptors: recent advances and new clinical potentials", Pharmaceutica Acta Helvetiae, 74, 2000, pp. 211-218.
Hanner, Markus, et al., "Purification, molecular cloning, and expression of the mammalian sigma1-binding site", Proc. Natl. Acad. Sci. USA, vol. 93, Jul. 1996, pp. 8072-8077.
Hayashi, T., et al., "The sigma-1 receptor and its role in the treatment of mood disorders", Drugs of the Future, 34(2), 2009, pp. 137-146.
International Search Report for PCT/EP2014/066223 dated Oct. 7, 2014.
Izquierdo, Sandra, et al., "(+)- and (−)-2-Aminocyclobutane-1-carboxylic acids and their incorporation into highly rigid β-peptides: stereoselective synthesis and a structural study", J. Org. Chem., 70, 2005, pp. 7963-7971.
Kaiser, et al., "Binding to the sigma receptor", Neurotransmissions, 7(1), 1991, pp. 1-5.
Quirion, Remi, et al., "A proposal for the classification of sigma binding sites", TiPS, vol. 13, Mar. 1992, pp. 85-86.
Ronsisvalle, Giuseppe, et al., "Opioid and sigma receptor studies. New developments in the design of selective sigma ligands", Pure Appl. Chem., vol. 73, No. 9, 2001, pp. 1499-1509.
Snyder, Solomon, H., et al., "Receptor mechanisms in antipsychotic drug action: focus on sigma receptors", Neuropsychiatry, 1989, pp. 1-7.
Torres, Elisabeth, et al., "Synthesis and structural study of novel dimethylcyclobuty β-peptides", Tetrahedron, 65, 2009, pp. 5669-5675.
Walker, J. Michael, et al., "Sigma receptors: biology and function", Pharmacological Reviews, vol. 42, No. 4, 1990, pp. 355-402.

* cited by examiner

*Primary Examiner* — Yong Chu
(74) *Attorney, Agent, or Firm* — Hueschen and Sage

(57) ABSTRACT

The invention refers to compounds of general formula (I)

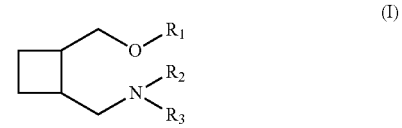

(I)

wherein the variables take various meanings, pharmaceutical compositions containing them and their use in medicine, particularly in pain therapy.

13 Claims, No Drawings

1,2-DISUBSTITUTED CYCLOBUTYL COMPOUNDS

FIELD OF THE INVENTION

The present invention relates to compounds, pharmaceutical compositions containing them and their use in medicine, particularly in pain therapy.

BACKGROUND

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF-10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection, psychosis and mood disorders [Kaiser et al (1991) Neurotransmissions 7 (1): 1-5], [Walker, J. M. et al, Pharmacological Reviews, 1990, 42, 355], [Bowen W. D. (2000) Pharmaceutica Acta Helvetiae 74: 211-218] and Hayashi, T. et al, Drugs of the Future 2009, 34 (2), 137].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Sigma-2 receptor ligands, specially agonists, can be used as antineoplastic agents at doses inducing apoptosis or at sub-toxic doses in combination with other antineoplastic agents to revert the resistance to the drug, thereby allowing using lower doses of the antineoplastic agent and considerably reducing its adverse effects.

Additionally, Sigma-2 receptor ligands, specially antagonists, can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find effective ligands. Different sigma receptor ligands have been reported.

For instance, WO2007/098961A1 describes 4,5,6,7-tetrahydrobenzo[b]thiophene derivatives having pharmacological activity towards the sigma receptor.

Spiro[benzopyran] and spiro[benzofuran] derivatives with pharmacological activity on sigma receptors are disclosed in WO2007/121976A1.

Pyrazole derivatives presenting a pyrazole group condensed with a cycloalkyl ring have been also reported as sigma ligands in WO2006/021463A1.

WO2008/055932A1 and WO2008/055933A1 deal with 1,2,4- and 1,2,3-triazole compounds, respectively, having activity towards sigma receptors.

WO2009/071657A1 also reports tricyclic triazolic compounds having activity towards sigma receptors.

WO2008/015266A1 discloses cyclobutyl compounds with sigma receptor binding.

In spite of this background, there is still a need to find further compounds that have pharmacological activity towards the sigma receptor, preferably being both effective and selective as well as having potentially good "drugability" properties, i.e. good pharmaceutical properties related to administration, distribution, metabolism and excretion.

BRIEF DESCRIPTION OF THE INVENTION

The present invention discloses novel 1,2-disubstituted cyclobutyl compounds with great affinity to sigma receptors which might be used for the treatment and/or prophylaxis of sigma related disorders or diseases.

Specifically, it is an object of the present invention a compound of general formula (I), or a pharmaceutically acceptable salt, isomer, prodrug or solvate thereof:

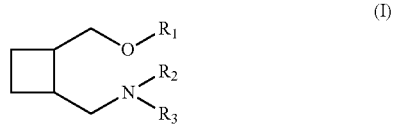

(I)

wherein
- R₁ is selected from the group consisting of substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heteroaryl, substituted or unsubstituted heteroarylalkyl, substituted or unsubstituted non-aromatic heterocyclyl, and substituted or unsubstituted non-aromatic heterocyclylalkyl;
- R₂ and R₃, identical or different, are selected from the group consisting of hydrogen, substituted or unsubstituted alkyl, substituted or unsubstituted cycloalkyl, substituted or unsubstituted cycloalkylalkyl, and substituted or unsubstituted alkenyl;
or
- R₂ and R₃ form together with the bridging nitrogen atom to which they are attached a substituted or unsubstituted non-aromatic heterocyclyl.

Another object of the invention refers to different processes for the preparation of a compound of general formula (I) as defined above, or a pharmaceutically acceptable salt, isomer, prodrug or solvate thereof.

Another object of the invention refers to a medicament or pharmaceutical composition comprising at least one compound of general formula (I) as defined above, or a pharmaceutically acceptable salt, isomer, prodrug or solvate thereof and at least one pharmaceutically acceptable excipient.

Another object of the invention refers to a compound of general formula (I) as defined above, or a pharmaceutically acceptable salt, isomer, prodrug or solvate thereof, for use as a medicament, particularly for the treatment and/or prophylaxis of a sigma receptor-mediated disease or condition.

Another object of the invention refers to the use of a compound of general formula (I) as defined above, or a pharmaceutically acceptable salt, isomer, prodrug or solvate thereof, in the manufacture of a medicament for the treatment and/or prophylaxis of a sigma receptor-mediated disease or condition.

Another object of the invention refers to a method for the treatment and/or prophylaxis of a sigma receptor-mediated disease or condition, the method comprising administering to the subject in need of such a treatment or prophylaxis a therapeutically effective amount of a compound of general formula (I) as defined above, or a pharmaceutically acceptable salt, isomer, prodrug or solvate thereof.

In one embodiment, said sigma receptor-mediated disease or condition is specifically a sigma-1 mediated disease or condition. Within the group of diseases or conditions mediated by sigma receptor for which the compounds of the invention are useful, the following may be cited: pain, diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, stroke including ischemic stroke, epilepsy, stress, cancer, psychotic conditions, in particular depression, anxiety or schizophrenia; inflammation or autoimmune diseases. According to one preferred embodiment, the compounds of the invention are used for the treatment and/or prophylaxis of pain, especially neuropathic pain, inflammatory pain or other pain conditions involving allodynia and/or hyperalgesia.

According to one preferred embodiment, the compounds of this invention effectively and selectively inhibit the Sigma-1 receptor. According to one more preferred embodiment, the compounds of the present invention are selective Sigma-1 antagonists.

These aspects and preferred embodiments thereof are additionally also defined hereinafter in the detailed description, as well as in the claims.

DETAILED DESCRIPTION OF THE INVENTION

In the context of the present invention, the following terms have the meaning detailed below.

"Alkyl" refers to a straight or branched hydrocarbon chain radical containing no unsaturation, and which is attached to the rest of the molecule by a single bond. Typical alkyl groups have from 1 to about 12, 1 to about 8, or 1 to about 6 carbon atoms, e.g., methyl, ethyl, n-propyl, i-propyl, n-butyl, t-butyl, n-pentyl, etc. If substituted by cycloalkyl, it corresponds to a "cycloalkylalkyl" radical, such as cyclopropyl methyl. If substituted by aryl, it corresponds to an "arylalkyl" radical, such as benzyl, benzhydryl or phenethyl. If substituted by heterocyclyl, it corresponds to a "heterocyclylalkyl" radical.

"Alkenyl" refers to a straight or branched hydrocarbon chain radical containing at least two carbon atoms and at least one unsaturation, and which is attached to the rest of the molecule by a single bond. Typical alkenyl radicals have from 2 to about 12, 2 to about 8 or 2 to about 6 carbon atoms. In a particular embodiment, the alkenyl group is vinyl, 1-methyl-ethenyl, 1-propenyl, 2-propenyl, or butenyl.

"Alkynyl" refers to a straight or branched hydrocarbon chain radical containing at least two carbon atoms and at least one carbon-carbon triple bond, and which is attached to the rest of the molecule by a single bond. Typical alkynyl radicals have from 2 to about 12, 2 to about 8 or 2 to about 6 carbon atoms. In a particular embodiment, the alkynyl group is ethynyl, propynyl (e.g. 1-propynyl, 2-propynyl), or butynyl (e.g. 1-butynyl, 2-butynyl, 3-butynyl).

"Cycloalkyl" refers to an alicyclic hydrocarbon. Typical cycloalkyl radicals contain from 1 to 4 separated and/or fused rings and from 3 to about 18 carbon atoms, preferably from 3 to 10 carbon atoms, such as cyclopropyl, cyclohexyl or adamantyl. In a particular embodiment, the cycloalkyl radical contains from 3 to about 6 carbon atoms.

"Aryl" refers to single and multiple ring radicals, including multiple ring radicals that contain separate and/or fused aryl groups. Typical aryl groups contain from 1 to 3 separated and/or fused rings and from 6 to about 18 carbon ring atoms, preferably from 6 to about 14 carbon ring atoms, such as phenyl, naphthyl, biphenyl, indenyl, fenanthryl or anthracyl radical.

"Heteroaryl" refers to heteroaromatic groups containing from 1 to 3 separated and/or fused rings and from 3 to about 18 ring atoms. Preferably heteroaromatic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl, and furopyridinyl.

"Non-aromatic Heterocyclyl" refers to heteroalicyclic groups containing from 1 to 3 separated and/or fused rings and from 3 to about 18 ring atoms. Preferably heteroalicyclic groups contain from 5 to about 10 ring atoms. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, azepinyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', SO$_2$R', OSO$_2$R', OSO$_3$R', NO$_2$, NHR', N(R')$_2$, =N—R', N(R')COR', N(COR)$_2$, N(R')SO$_2$R', N(R')C(=NR')N(R')R', N$_3$, CN, halogen, COR', COOR', OCOR', OCOOR', OCONHR', OCON(R')$_2$, CONHR', CON(R')$_2$, PO(OR')$_2$, PO(OR')R', C$_1$-C$_{12}$ alkyl, C$_3$-C$_{10}$ cycloalkyl, C$_2$-C$_{12}$ alkenyl, C$_2$-C$_{12}$ alkynyl, aryl, heteroaryl and non-aromatic heterocyclic group, wherein each of the R' groups is independently selected from the group consisting of hydrogen, OH, NH$_2$, SH, CN, halogen, COH, COalkyl, COOH, C$_1$-C$_{12}$ alkyl, C$_3$-C$_{10}$ cycloalkyl, C$_2$-C$_{12}$ alkenyl, C$_2$-C$_{12}$ alkynyl, aryl, heteroaryl and non-aromatic heterocyclic group.

"Halogen", "halo" or "hal" refers to bromo, chloro, iodo or fluoro.

The term "salt" must be understood as any form of a compound used in accordance with this invention in which said compound is in ionic form or is charged and coupled to a counter-ion (a cation or anion) or is in solution. This definition also includes quaternary ammonium salts and complexes of the molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention normally an acid (deprotonated) such as an anion and at least one physiologically tolerated cation, preferably inorganic, particularly when used on humans and/or mammals. Salts with alkali and alkali earth metals are preferred particularly, as well as those formed with ammonium cations (NH$_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As used herein, the terms "treat", "treating" and "treatment" include the eradication, removal, reversion, alleviation, modification, or control of a disease or condition after its onset.

As used herein, the terms "prevention", "preventing", "preventive" "prevent" and "prophylaxis" refer to the capacity of a therapeutic to avoid, minimize or difficult the onset or development of a disease or condition before its onset.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated. As such, the method of the present invention also includes situations where the condition is completely inhibited, e.g., prevented from happening, or stopped, e.g., terminated, such that the subject no longer experiences the condition.

The inventors of the present invention have observed that 1,2-disubstituted cyclobutyl compounds with general formula (I) as defined above unexpectedly show an affinity for Sigma-1 receptor ranging from good to excellent. These compounds are therefore particularly suitable as pharmacologically active agents in medicaments for the prophylaxis and/or treatment of disorders or diseases related to Sigma receptors, preferably related to Sigma-1 receptor.

All the diastereoisomers of general formula (I), as depicted below are included within the scope of the invention.

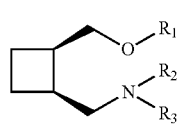

(Ia)

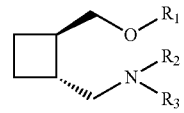

(Ib)

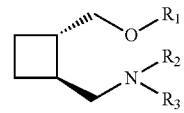

(Ic)

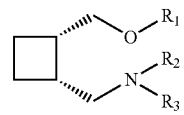

(Id)

In a preferred embodiment the compounds of the invention are compounds according to general formula (Ia).

In another preferred embodiment the compounds of the invention are compounds according to general formula (Ib).

In another preferred embodiment the compounds of the invention are compounds according to general formula (Ic).

In another preferred embodiment the compounds of the invention are compounds according to general formula (Id).

In a particular embodiment, $R_1$ in the compounds of general formula (I) is selected from the group consisting of substituted or unsubstituted aryl and substituted or unsubstituted heteroaryl.

In a more particular embodiment, $R_1$ is selected from the group consisting of substituted or unsubstituted $C_6$-$C_{14}$ aryl and substituted or unsubstituted 5- to 10-membered heteroaryl.

In preferred variants of the invention, $R_1$ is substituted or unsubstituted $C_6$-$C_{14}$ aryl, more preferably substituted or unsubstituted phenyl. Preferred substituents for the aryl groups representing $R_1$ are halogen such as chloro.

In preferred variants of the invention, $R_1$ is substituted or unsubstituted 5- to 10-membered heteroaryl (i.e. an heteroaromatic group), more preferably substituted or unsubstituted pyrazole. Preferred substituents for the heterocyclyl groups representing $R_1$ are halogen (preferably chloro), methyl, trifluoromethyl, optionally substituted aryl (preferably phenyl, which may be optionally substituted for instance with halogen such as chloro).

In a particular embodiment, $R_1$ in the compounds of general formula (I) is selected from the group consisting of:

-continued

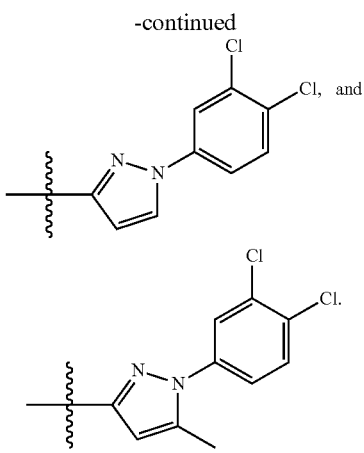

In a particular embodiment $R_2$ and $R_3$ are independently selected from the group consisting of hydrogen, substituted or unsubstituted alkyl, and substituted or unsubstituted cycloalkyl, or $R_2$ and $R_3$ together with the bridging nitrogen atom form a substituted or unsubstituted non-aromatic heterocyclyl.

In a more particular embodiment, $R_2$ and $R_3$ are independently selected from the group consisting of hydrogen and substituted or unsubstituted $C_1$-$C_6$ alkyl, or $R_2$ and $R_3$ together with the bridging nitrogen atom form a substituted or unsubstituted 5- to 10-membered non-aromatic heterocyclyl, preferably a substituted or unsubstituted 5-, 6- or 7-membered non-aromatic heterocyclyl.

Preferably, $R_2$ and $R_3$ are independently selected from the group consisting of hydrogen and substituted or unsubstituted methyl or ethyl, or $R_2$ and $R_3$ together with the bridging nitrogen atom form a substituted or unsubstituted pyrrolidinyl, morpholinyl or piperidinyl, Particular heterocyclyl radicals formed by $R_2$ and $R_3$ together with the bridging nitrogen atom are pyrrolidinyl, morpholinyl and 4-methylpiperidinyl. Thus, in a particular embodiment, $R_2$ and $R_3$ in the compounds of general formula (I) together with the bridging nitrogen atom form a non-aromatic heterocyclyl selected from the group consisting of:

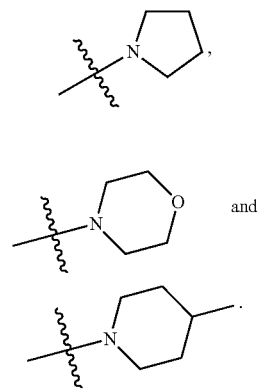

In additional preferred embodiments, the preferences described above for the different substituents are combined. The present invention is also directed to such combinations of preferred substitutions in the formula (I) above.

Particular individual compounds of the invention falling under formula (I) include the compounds listed below:

[1] 1-(((1S,2R)-2-(Phenoxymethyl)cyclobutyl)methyl)pyrrolidine

[2] 4-(((1S,2R)-2-(Phenoxymethyl)cyclobutyl)methyl)morpholine

[3] 4-methyl-1-(((1S,2R)-2-(Phenoxymethyl)cyclobutyl)methyl)piperidine

[4] 1-(((1S,2R)-2-((3,4-Dichlorophenoxy)methyl)cyclobutyl)methyl)pyrrolidine

[5] 4-(((1S,2R)-2-((3,4-Dichlorophenoxy)methyl)cyclobutyl)methyl)morpholine

[6] 1-(((1S,2R)-2-((3,4-Dichlorophenoxy)methyl)cyclobutyl)methyl)-4-methylpiperidine

[7] 4-Methyl-1-(((1S,2R)-2-(((1-methyl-5-(trifluoromethyl)-1H-pyrazol-3-yl)oxy)methyl)cyclobutyl)methyl)piperidine

[8] 4-Methyl-1-(((1S,2R)-2-(((1-methyl-3-(trifluoromethyl)-1H-pyrazol-5-yl)oxy)methyl)cyclobutyl)methyl)piperidine

[9] 1-Methyl-3-(((1R,2S)-2-(pyrrolidin-1-ylmethyl)cyclobutyl)methoxy)-5-(trifluoromethyl)-1H-pyrazole

[10] 4-(((1S,2R)-2-(((1-Methyl-5-(trifluoromethyl)-1H-pyrazol-3-yl)oxy)methyl)cyclobutyl)methyl)morpholine

[11] 1-Methyl-5-(((1R,2S)-2-(pyrrolidin-1-ylmethyl)cyclobutyl)methoxy)-3-(trifluoromethyl)-1H-pyrazole

[12] 4-(((1S,2R)-2-(((1-Methyl-3-(trifluoromethyl)-1H-pyrazol-5-yl)oxy)methyl)cyclobutyl)methyl)morpholine

[13] 1-(3,4-Dichlorophenyl)-3-(((1R,2S)-2-(pyrrolidin-1-ylmethyl)cyclobutyl) methoxy)-1H-pyrazole

[14] 4-(((1S,2R)-2-(((1-(3,4-Dichlorophenyl)-1H-pyrazol-3-yl)oxy)methyl)cyclobutyl)methyl)morpholine

[15] 1-(3,4-Dichlorophenyl)-5-methyl-3-(((1R,2S)-2-(pyrrolidin-1-ylmethyl)cyclobutyl) methoxy)-1H-pyrazole

[16] 4-(((1S,2R)-2-(((1-(3,4-Dichlorophenyl)-5-methyl-1H-pyrazol-3-yl)oxy)methyl)cyclobutyl)methyl)morpholine

[17] 4-(((1S,2R)-2-(Phenoxymethyl)cyclobutyl)methyl)morpholine hydrochloride

[18] 1-(((1S,2R)-2-((3,4-Dichlorophenoxy)methyl)cyclobutyl)methyl)pyrrolidine hydrochloride

[19] 4-(((1S,2R)-2-((3,4-Dichlorophenoxy)methyl)cyclobutyl)methyl)morpholine hydrochloride

[20] 1-(((1S,2R)-2-((3,4-dichlorophenoxy)methyl)cyclobutyl)methyl)-4-methylpiperidine hydrochloride

[21] 1-Methyl-3-(((1R,2S)-2-(pyrrolidin-1-ylmethyl)cyclobutyl)methoxy)-5-(trifluoromethyl)-1H-pyrazole hydrochloride

[22] 4-(((1S,2R)-2-(((1-methyl-5-(trifluoromethyl)-1H-pyrazol-3-yl)oxy)methyl)cyclobutyl)methyl)morpholine hydrochloride

[23] 1-Methyl-5-(((1R,2S)-2-(pyrrolidin-1-ylmethyl)cyclobutyl)methoxy)-3-(trifluoromethyl)-1H-pyrazole hydrochloride

[24] 4-(((1S,2R)-2-(((1-Methyl-3-(trifluoromethyl)-1H-pyrazol-5-yl)oxy)methyl)cyclobutyl)methyl)morpholine hydrochloride

[25] 1-(3,4-Dichlorophenyl)-3-(((1R,2S)-2-(pyrrolidin-1-ylmethyl)cyclobutyl)methoxy)-1H-pyrazole hydrochloride

[26] 4-(((1S,2R)-2-(((1-(3,4-Dichlorophenyl)-1H-pyrazol-3-yl)oxy)methyl)cyclobutyl)methyl)morpholine hydrochloride

[27] 1-(3,4-Dichlorophenyl)-5-methyl-3-(((1R,2S)-2-(pyrrolidin-1-ylmethyl)cyclobutyl)methoxy)-1H-pyrazole hydrochloride
[28] 1-(3,4-Dichlorophenyl)-3-(((1R,2R)-2-(pyrrolidin-1-ylmethyl)cyclobutyl) methoxy)-1H-pyrazole
[29] 1-(3,4-Dichlorophenyl)-5-methyl-3-(((1R,2R)-2-(pyrrolidin-1-ylmethyl)cyclobutyl) methoxy)-1H-pyrazole
[30] 4-(((1R,2R)-2-(((1-(3,4-Dichlorophenyl)-5-methyl-1H-pyrazol-3-yl)oxy)methyl)cyclobutyl)methyl)morpholine
[31] 1-Methyl-3-(((1R,2R)-2-(pyrrolidin-1-ylmethyl)cyclobutyl)methoxy)-5-(trifluoromethyl)-1H-pyrazole
[32] 1-Methyl-3-(((1R,2R)-2-(pyrrolidin-1-ylmethyl)cyclobutyl)methoxy)-5-(trifluoromethyl)-1H-pyrazole hydrochloride
[33] 1-Methyl-3-(((1S,2R)-2-(pyrrolidin-1-ylmethyl)cyclobutyl)methoxy)-5-(trifluoromethyl)-1H-pyrazole
[34] 1-Methyl-3-(((1S,2R)-2-(pyrrolidin-1-ylmethyl)cyclobutyl)methoxy)-5-(trifluoromethyl)-1H-pyrazole hydrochloride
[35] 1-Methyl-3-(((1S,2S)-2-(pyrrolidin-1-ylmethyl)cyclobutyl)methoxy)-5-(trifluoromethyl)-1H-pyrazole
[36] 4-(((1S,2S)-2-(((1-(3,4-Dichlorophenyl)-5-methyl-1H-pyrazol-3-yl)oxy)methyl)cyclobutyl)methyl)morpholine
[37] N,N-Diethyl-N-(((1S,2S)-2-(phenoxymethyl)cyclobutyl)methyl)ethanamine
[38] 1-methyl-3-(((1S,2S)-2-(pyrrolidin-1-ylmethyl)cyclobutyl)methoxy)-5-(trifluoromethyl)-1H-pyrazole hydrochloride
[39] N,N-Diethyl-N-(((1S,2S)-2-(phenoxymethyl)cyclobutyl)methyl)ethanamine hydrochloride or a solvate or prodrug thereof as well as any pharmaceutically acceptable salt of the free-base compounds.

The compounds of general formula (I) and the corresponding diastereoisomers above disclosed (Ia, Ib, Ic and/or Id) can be obtained by available synthetic procedures. For instance, they can be prepared in accordance with the following general procedures.

Synthesis of (R,S)-Stereoisomers

Compounds of General Formula (Ia) (Scheme 1)

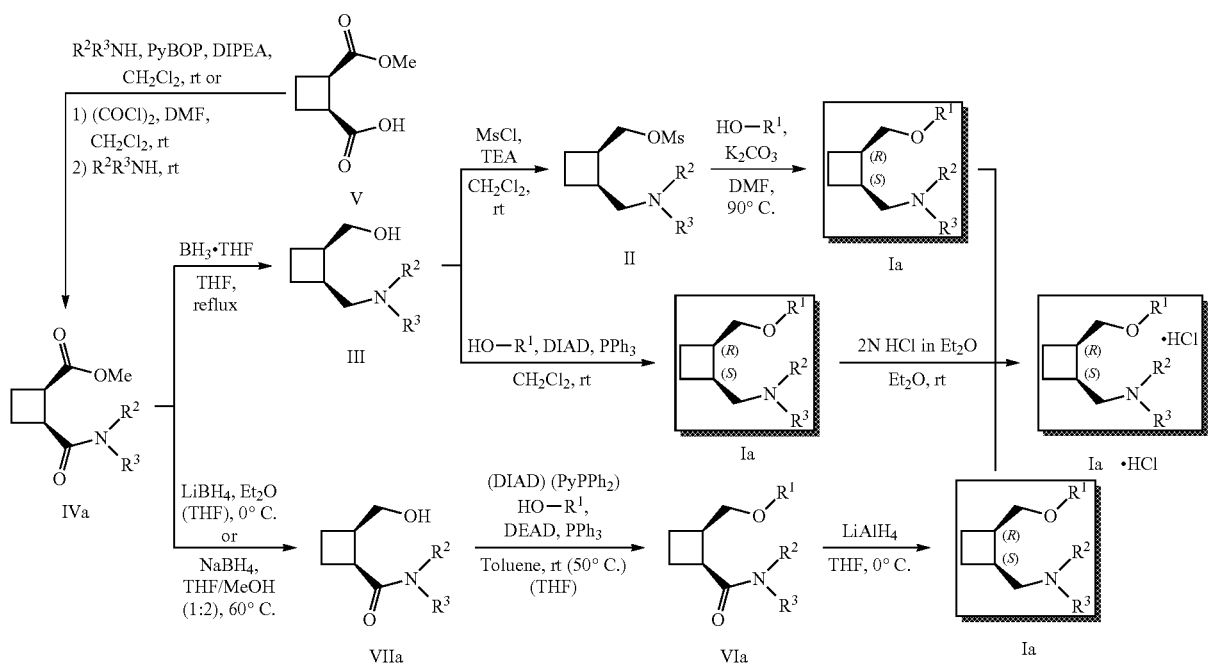

Scheme 1

Compounds of general formula (Ia) can be prepared through reactions of mesylates II with aromatic alcohols R$^1$OH in the presence of potassium carbonate as a base and DMF (dimethylformamide) as a solvent. In turn, mesylates can be prepared by reaction of alcohols III with mesyl chloride and triethylamine. Alcohols III come from total reduction of compounds IVa with BH$_3$ in refluxing THF (tetrahydrofuran). Compound IVa is prepared from half ester V, which is synthesized according to S. Izquierdo, F. Rúa, A. Sbai. T. Parella, Á. Álvarez-Larena, V. Branchadell, R. M. Ortuño, *J. Org. Chem.* 2005, 70, 7963-7971. Compound IVa is obtained from V by standard peptide coupling procedures, i.e., reaction with a secondary amine R$^2$R$^3$NH in the presence of PyBOP (benzotriazol-1-yl-oxytripyrrolidinophosphonium hexafluorophosphate) and DIPEA (N,N-diisopropiletilamina) or, alternatively, via acyl chloride prepared by reaction of V with oxalyl chloride and in situ reaction with the amine.

Alternatively, compounds of general formula (Ia) can be synthesized via a Mitsunobu reaction between alcohols III and an aromatic alcohol R$^1$OH in the presence of DIAD (diisopropyl azodicarboxylate) and PPh$_3$.

A third alternative route to synthesize compounds of general formula (Ia) consists in reduction of amides VIa with LiAlH$_4$ in THF at 0° C. Amides VIa come from Mitsunobu reaction of alcohols VIa with aromatic alcohols R$^1$OH in the presence DIAD/PyPPh$_2$ (PyPPh$_2$: 2-pyridyldiphenylphosphine) or DEAD/PPh$_3$ (DEAD: diethyl azodicarboxylate). Alcohols VIa are prepared by selective reduction of the methyl ester IVa by using LiBH$_4$ in Et$_2$O or THF at 0° C., or NaBH$_4$ in THF-MeOH.

Synthesis of (R,R)-Stereoisomers

Compounds of General Formula (Ib) (Scheme 2)

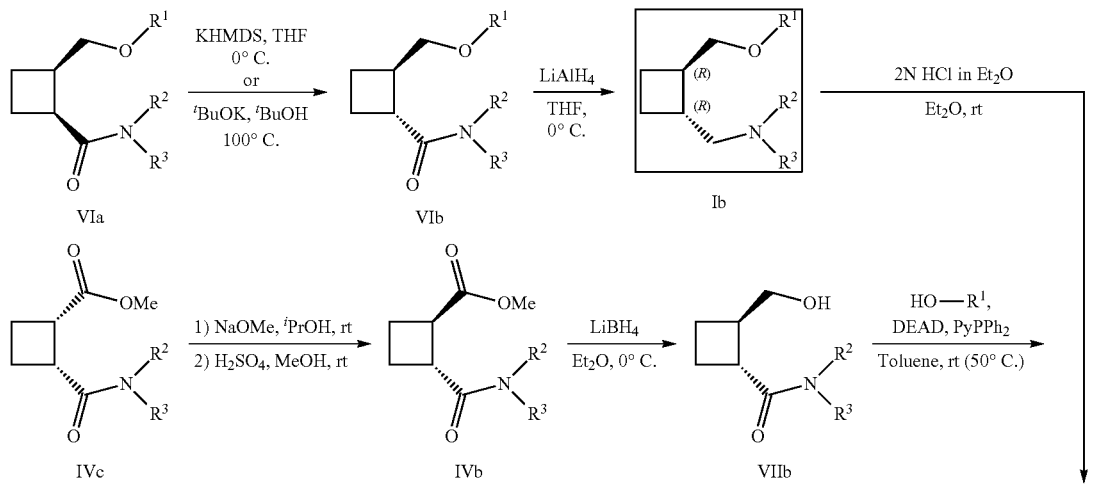

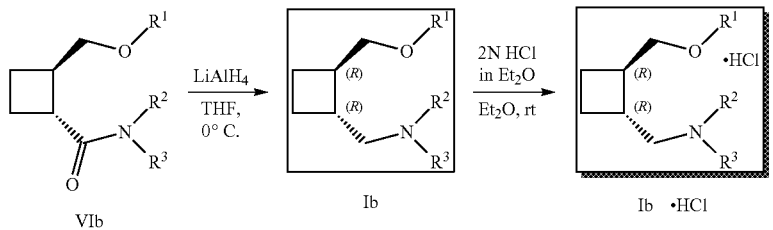

Compounds of general formula (Ib) result from reduction of amides VIb with LiAlH$_4$. Amides VIb are obtained through epimerization of VIa by using KHMDS (potassium hexamethyldisilazane) in THF at 0° C. or $^t$BuOK in $^t$BuOH at 100° C.

Alternatively, compounds of general formula (Ib) can be prepared through the reduction of amides VIb with LiAlH$_4$ in THF at 0° C. Compounds VIb result from Mitsunobu reaction of alcohols VIIb with aromatic alcohols R$^1$OH in the presence of DEAD and PyPPh$_2$. Alcohols VIIb result from selective reduction of the methyl ester in IVb with LiBH$_4$ in Et$_2$O at 0° C. Compound IVb is prepared through epimerization of IVc with MeONa in $^i$PrOH followed by treatment with H$_2$SO$_4$ in MeOH.

Compound IVc is synthesized from amino ester VIII (Scheme 3) by elimination of the tert-butyl ester with TFA (trifluoroacetic acid) and subsequent Fisher esterification of the resulting acid with MeOH and H$_2$SO$_4$. Compound VIII is obtained by peptide coupling of R$^1$R$^2$NH secondary amines (PyBOP, DIPEA) with acid IX, which is prepared as previously described in S. Izquierdo, F. Rúa, A. Sbai. T. Parella, Á. Álvarez-Larena, V. Branchadell, R. M. Ortuño, *J. Org. Chem.* 2005, 70, 7963-7971.

Scheme 3

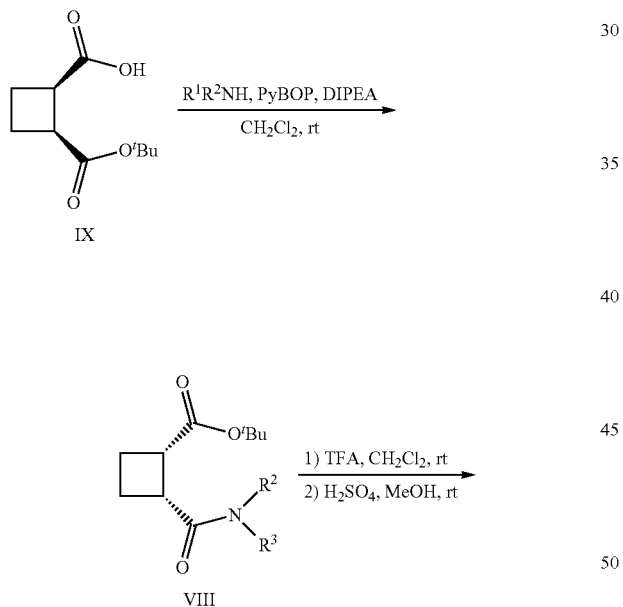

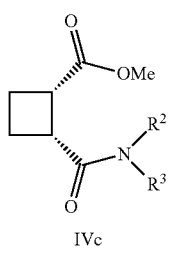

IVc

Synthesis of (S,R)-Stereoisomers

Compounds of General Formula (Ic) (Scheme 4)

Scheme 4

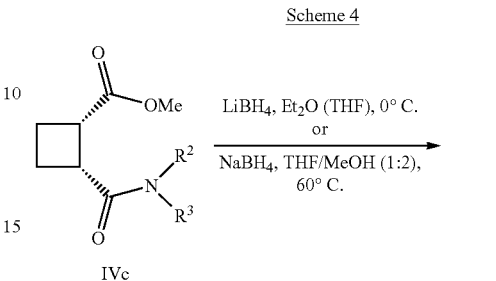

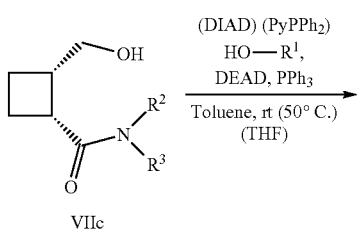

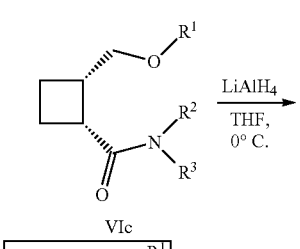

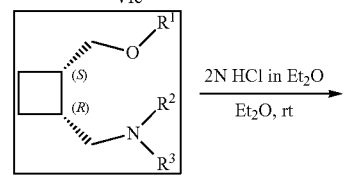

This route is similar to one of the synthetic pathways in Scheme 1 to prepare compounds of general formula (Ia). Compounds of general formula (Ic) result from reduction of amides VIc with LiAlH$_4$ in THF at 0° C. Amides VIc are obtained through Mitsunobu reaction of alcohols VIIc with aromatic alcohol R$^1$OH in the presence of DIAD/PyPPh$_2$ or DEAD/PPh$_3$. Alcohols VIIc are prepared by selective reduction of the methyl ester IVc by using LiBH$_4$ in Et$_2$O or THF at 0° C., or NaBH$_4$ in THF-MeOH.

Synthesis of (S,S)-Stereoisomers

Compounds of General Formula (Id) (Scheme 5)

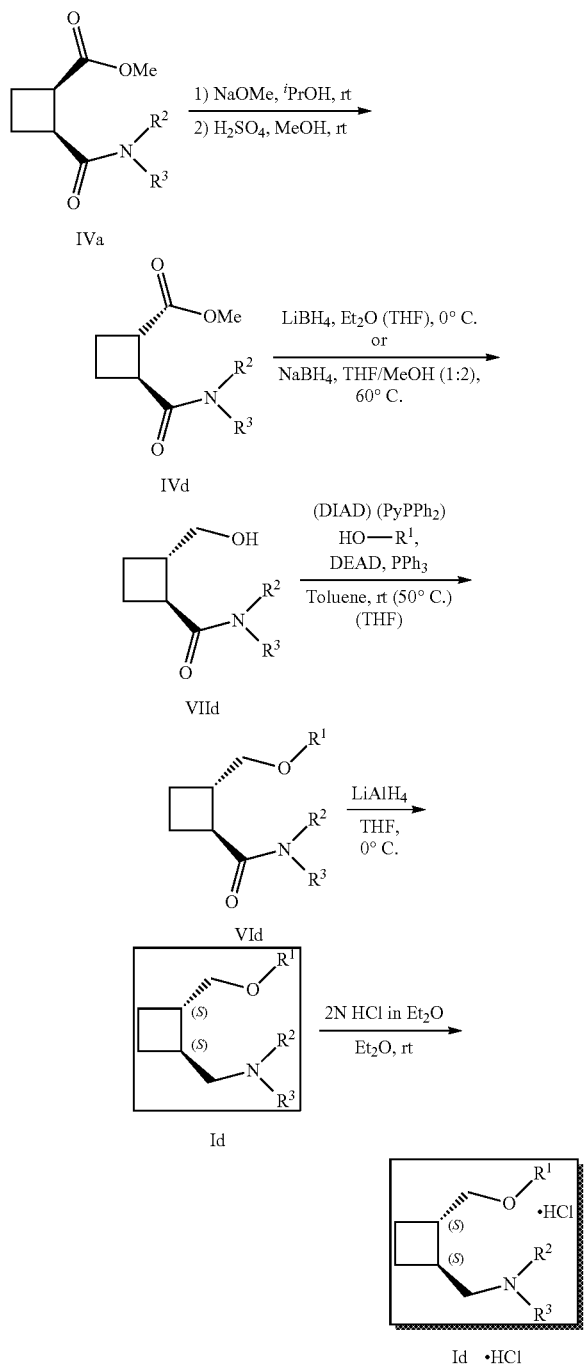

The synthesis is similar than that depicted in Scheme 2 for (R,R)-compounds Ib. Compounds of general formula (Id) can be prepared through the reduction of amides VId with LiAlH$_4$ in THF at 0° C. Compounds VId result from Mitsunobu reaction of alcohols VIId with aromatic alcohol R$^1$OH, in the presence of DEAD and PyPPh$_2$. Alcohols VIId result from selective reduction of the methyl ester in IVd with LiBH$_4$ in Et$_2$O at 0° C. Compound IVd is prepared through epimerization of IVa with MeONa in $^i$PrOH followed by treatment with H$_2$SO$_4$ in MeOH.

Additionally, the processes defined above may include the transformation of any compound (starting, intermediate or final) in a salt thereof. In a particular embodiment the processes further comprise the transformation of the compound of general formula (I) or its corresponding diastereoisomers (Ia, Ib, Ic and/or Id) obtained in a salt thereof such as the HCl salt. For example, the hydrochloride salts Ia.HCl, Ib.HCl, Ic.HCl and Id.HCl can be prepared by treatment of the corresponding amines with 2N HCl in Et$_2$O.

It is also an object of the invention to provide medicaments or pharmaceutical compositions comprising at least one compound of general formula (I) as defined above, or a pharmaceutically acceptable salt, isomer, prodrug or solvate thereof, and at least one pharmaceutically acceptable excipient.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application. The preferred form of rectal application is by means of suppositories.

Suitable preparations for oral applications are tablets, pills, chewing gums, capsules, granules, drops or syrups. Suitable preparations for parenteral applications are solutions, suspensions, reconstitutable dry preparations or sprays.

The pharmaceutical composition of the invention may be formulated as deposits in dissolved form or in patches, for percutaneous application. Skin applications include ointments, gels, creams, lotions, suspensions or emulsions.

Another aspect of the invention is a method for the treatment and/or prophylaxis of a sigma receptor-mediated disease or condition, the method comprising administering to the subject in need of such a treatment or prophylaxis a therapeutically effective amount of a compound of formula (I) as defined above, or a pharmaceutically acceptable salt, isomer, prodrug or solvate thereof.

Generally an effective administered amount of a compound used in the invention will depend on the relative efficacy of the compound chosen, the severity of the disorder being treated, or the age, weight or mode of administration. However, active compounds will typically be administered once or more times a day, for example 1, 2, 3 or 4 times daily, with typical total daily doses in the range of from 0.1 to 500 mg/kg/day.

Having described the present invention in general terms, it will be more easily understood by reference to the following examples which are presented as an illustration and are not intended to limit the present invention.

EXAMPLES

Synthesis of (R,S)-Stereoisomers

Compounds of General Formula (Ia) According to the Synthetic Pathway Disclosed in Scheme no 1

Half-ester V was prepared according to the previous procedure published in: S. Izquierdo, F. Rúa, A. Sbai. T. Parella, Á. Álvarez-Larena, V. Branchadell, R. M. Ortuño, *J. Org. Chem.* 2005, 70, 7963-7971.

Coupling of the Amine Via Acid Chloride: Compounds IVa.

Under N$_2$ atmosphere, half-ester is dissolved in dichloromethane (0.1 M) at room temperature, followed by the addition of oxalyl chloride (1.1 eq., 2M in CH$_2$Cl$_2$) and a few drops DMF. The resulting mixture is stirred for 2 h and then pyrrolidine (3.0 eq.) is added. The reaction is allowed to evolve overnight.

After the specified time, HCl 2M (3.0 eq.) is added and the solution is stirred for 20 min. Then, more dichloromethane and water are added and the phases are separated. The organic phase is washed with saturated aqueous solution of NaHCO$_3$ and brine, dried and evaporated under reduced pressure, to afford the final products as oils. (yield: 81-88%).

According to this procedure, the following compounds IVa were synthesized:

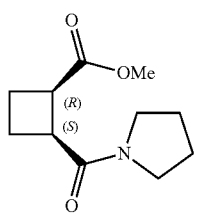

(1R,2S)-Methyl-2-(pyrrolidine-1-carbonyl)cyclobutanecarboxylate (yield: 88%)

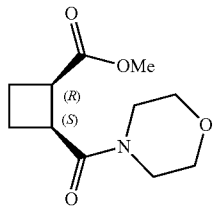

(1R,2S)-Methyl-2-(morpholine-4-carbonyl)cyclobutanecarboxylate (yield: 86%)

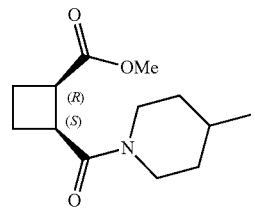

(1R,2S)-Methyl-2-(4-methylpiperidine-1-carbonyl)cyclobutanecarboxylate (yield: 81%)

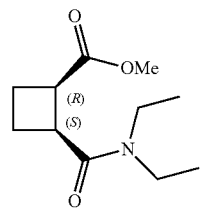

(1R,2S)-Methyl 2-(diethylcarbamoyl)cyclobutanecarboxylate (yield: 82%)

Reduction of IVa with Borane: Synthesis of Amino Alcohols III.

Amido ester IVa is dissolved in THF (0.5 M) and borane in THF solution (6 eq) is added slowly via syringe. Then the system is heated to reflux. After TLC completion (2-4 hour), the system is cooled at room temperature and MeOH is added very slowly. The crude is evaporated and washed with CH$_2$Cl$_2$, AcOEt and water. The organic layer is dried over MgSO$_4$ and the solvents are removed to afford the corresponding amino alcohols III as colourless oils. (yield: 66-70%)

According to this procedure, the following compounds III were synthesized:

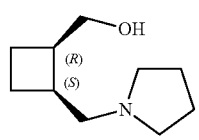

((1R,2S)-2-(Pyrrolidin-1-ylmethyl)cyclobutyl)methanol (yield: 70%)

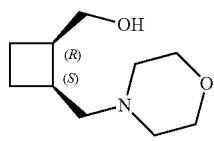

((1R,2S)-2-(Morpholinomethyl)cyclobutyl)methanol (yield: 69%)

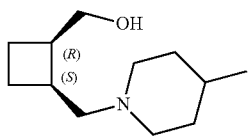

((1R,2S)-2-((4-Methylpiperidin-1-yl)methyl)cyclobutyl) methanol (yield: 66%)

Mesylation of Alcohols III: Synthesis of Mesylates II.

The corresponding alcohol is dissolved in dichloromethane (0.1 M) and the solution cooled down to 0° C. with an ice bath. Then, are sequentially added triethylamine (2.0 eq.), DMAP (0.2 eq.) and, dropwise, MsCl (2.0 eq.). The mixture is stirred at this temperature for 2 h, when TLC analysis showed totally consumption of the starting material.

At this moment, water is added and the phases separated, extracting the aqueous phase with more dichloromethane. The whole organic layers are dried and evaporated under reduced pressure to afford the corresponding mesylates, which were used in the next step without further purification.

According to this procedure, the following compounds II were synthesized:

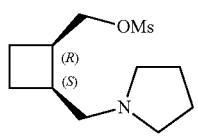

((1R,2S)-2-(Pyrrolidin-1-ylmethyl)cyclobutyl)methyl methanesulfonate

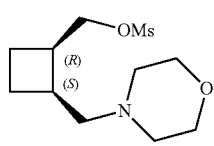

((1R,2S)-2-(Morpholinomethyl)cyclobutyl)methyl methanesulfonate

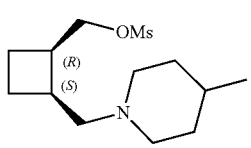

((1R,2S)-2-((4-Methylpiperidin-1-yl)methyl)cyclobutyl) methyl methanesulfonate $S_N2$ Reaction of Mesylates II with Phenol: Synthesis of Compounds of General Formula (Ia) (Examples 1-3)

Mesylate II is dissolved in DMF (0.1 M) under nitrogen atmosphere and aromatic alcohol (2.0 eq.) and potassium carbonate (3.0 eq.) are added. The mixture is heated to 80° C. and stirred overnight. Next day, water is added and the aqueous phase extracted with diethyl ether. The whole organic layers are dried and evaporated under reduced pressure to afford crude oil. Purification was achieved by flash column chromatography on silica gel providing compounds (la) as colourless oils (Examples 1-3). (yield: 44-53%)

According to this procedure, the following compounds of general formula (Ia) were synthesized:

Example 1

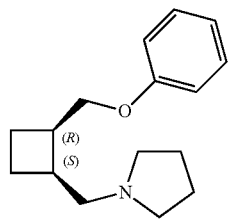

1-(((1S,2R)-2-(Phenoxymethyl)cyclobutyl)methyl)pyrrolidine (yield: 53%)

$^1$H NMR (360 MHz, CDCl$_3$) δ 7.30 (m, 2H), 6.94 (m, 3H), 4.04 (t, J=7.0 Hz, 2H), 2.86 (d, J=10.0 Hz, 2H), 2.77 (m, 2H), 2.55 (t, J=7.5 Hz, 2H), 2.14 (m, 2H), 2.03 (m, 2H), 1.91 (m, 2H), 1.76 (m, 4H).

Example 2

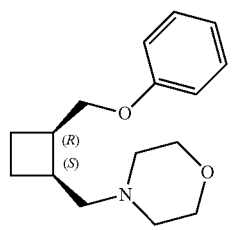

4-(((1S,2R)-2-(Phenoxymethyl)cyclobutyl)methyl)morpholine (yield: 44%)

$^1$H NMR (360 MHz, CDCl$_3$) δ 7.28 (dd, J=8.6, 7.5 Hz, 2H), 6.99-6.82 (m, 3H), 4.16 (dd, J=9.3, 6.8 Hz, 1H), 4.01 (dd, J=9.4, 6.4 Hz, 1H), 3.67 (t, J=4.7 Hz, 4H), 2.81 (dd, J=5.1, 2.9 Hz, 2H), 2.64 (dd, J=12.3, 6.4 Hz, 1H), 2.52-2.29 (m, 4H), 2.24-2.02 (m, 2H), 1.82 (dd, J=8.6, 3.8 Hz, 2H).

Example 3

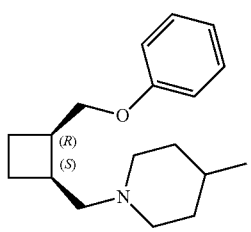

4-Methyl-1-(((1S,2R)-2-(phenoxymethyl)cyclobutyl)methyl)piperidine (yield: 51%)

$^1$H NMR (360 MHz, CDCl$_3$) δ 7.30 (m, 2H), 6.94 (m, 3H), 4.19 (dd, J=9.0, 6.0 Hz, 1H), 4.03 (dd, J=9.0, 6.0 Hz, 1H), 2.82 (m, 4H), 2.63 (dd, J=12.0, 6.0 Hz, 1H), 2.14 (m, 2H), 1.91 (m, 4H), 1.61 (m, 2H), 1.26 (m, 3H), 0.92 (d, J=6.0 Hz, 3H).

Mitsunobu Reaction

Synthesis of Compounds of General Formula (Ia) (Examples 4-8)

Starting primary alcohol, the corresponding ArOH (1.2 eq) and triphenylphosphine (1.5 eq) are dissolved in toluene (0.12 mM) under nitrogen atmosphere and the reaction is cooled to 0° C. with an ice bath. After five minutes of stirring, a 40% solution of DEAD (diethyl azodicarboxylate) in toluene (1.5 eq) is added dropwise during 10 minutes and the mixture is heated to 50° C. and stirred for 2 h. The reaction can also be carried out with DIAD (diisopropyl azodicarboxylate) as the azoderivative, and in dichloromethane or THF as the solvent.

Once the reaction has come to an end, the crude mixture is set inside the fridge overnight and the resulting white precipitate is filtered off. The filtrate is evaporated under reduced pressure and the remaining orange oil is purified by flash column chromatography in silica gel (hexanes/EtOAc 6:1 to 3:1) affording the desired products as colourless oils (yield: 56-77%).

According to this procedure, the following compounds of general formula (Ia) were synthesized:

Example 4

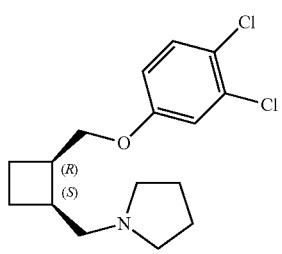

1-(((1S,2R)-2-((3,4-Dichlorophenoxy)methyl)cyclobutyl)methyl)pyrrolidine (yield: 73%)

$^1$H NMR (360 MHz, CDCl$_3$) δ 7.32 (d, J=8.8 Hz, 1H), 7.00 (s, 1H), 6.76 (d, J=8.8 Hz, 1H), 3.99 (t, J=6.2 Hz, 2H), 2.90 (d, J=9.3 Hz, 2H), 2.79 (s, 2H), 2.57 (t, J=7.3 Hz, 2H), 2.23-2.03 (m, 4H), 1.88 (dt, J=12.7, 6.4 Hz, 2H), 1.75 (s, 4H).

Example 5

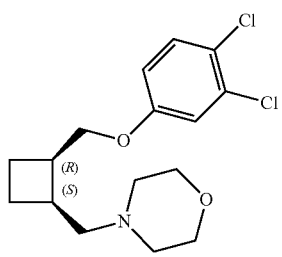

4-(((1S,2R)-2-((3,4-Dichlorophenoxy)methyl)cyclobutyl)methyl)morpholine (yield: 77%)

$^1$H NMR (360 MHz, CDCl$_3$) δ 7.34 (d, J=8.9 Hz, 1H), 7.02 (d, J=2.8 Hz, 1H), 6.78 (dd, J=8.9, 2.9 Hz, 1H), 4.31-4.02 (m, 4H), 3.74-3.60 (m, 2H), 3.37 (dd, J=11.5, 6.5 Hz, 1H), 3.09 (dd, J=12.8, 4.3 Hz, 1H), 2.97-2.59 (m, 6H), 2.22 (ddd, J=20.1, 10.6, 4.5 Hz, 2H), 2.08 (dd, J=16.2, 6.3 Hz, 1H), 1.72 (t, J=10.1 Hz, 1H).

Example 6

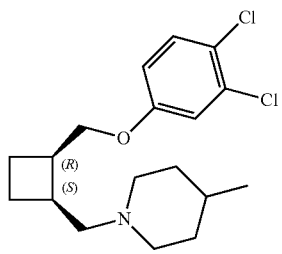

1-(((1S,2R)-2-((3,4-Dichlorophenoxy)methyl)cyclobutyl)methyl)-4-methylpiperidine (yield: 69%)

$^1$H NMR (250 MHz, CDCl$_3$) δ 7.33 (d, J=8.9 Hz, 1H), 7.02 (d, J=2.8 Hz, 1H), 6.77 (dd, J=8.9, 2.9 Hz, 1H), 4.08 (ddd, J=41.3, 9.2, 6.5 Hz, 2H), 2.82 (dd, J=12.2, 9.7 Hz, 4H), 2.58 (dd, J=12.4, 6.2 Hz, 1H), 2.31 (dd, J=12.5, 7.2 Hz, 1H), 2.14 (dt, J=9.5, 5.1 Hz, 2H), 1.99-1.72 (m, 4H), 1.60 (d, J=12.6 Hz, 2H), 1.29 (m, 4H), 0.91 (d, J=6.0 Hz, 3H).

Example 7

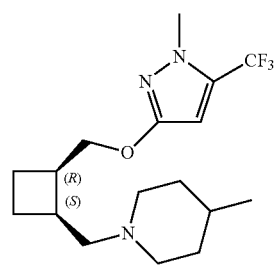

4-Methyl-1-(((1S,2R)-2-(((1-methyl-5-(trifluoromethyl)-1H-pyrazol-3-yl)oxy)methyl) cyclobutyl)methyl)piperidine (yield: 71%)

$^1$H NMR (360 MHz, Acetone-$d_6$) δ 6.22 (d, J=10.8 Hz, 1H), 4.52-4.37 (m, 1H), 4.30 (dt, J=10.5, 6.5 Hz, 1H), 3.86 (d, J=4.2 Hz, 3H), 3.38-3.10 (m, 4H), 3.10-2.66 (m, 5H), 2.33-2.10 (m, 3H), 1.71 (dd, J=11.5, 4.5 Hz, 2H), 1.67-1.42 (m, 4H), 0.97 (d, J=5.6 Hz, 3H).

Example 8

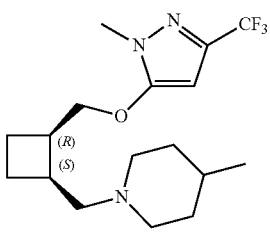

4-Methyl-1-(((1S,2R)-2-(((1-methyl-3-(trifluoromethyl)-1H-pyrazol-5-yl)oxy)methyl) cyclobutyl)methyl)piperidine (yield: 56%)

$^1$H NMR (250 MHz, CDCl$_3$) δ 5.86 (s, 1H), 4.44-4.20 (m, 2H), 3.73 (s, 3H), 3.09-2.91 (m, 4H), 2.79 (dd, J=12.9, 4.7 Hz, 2H), 2.52-2.30 (m, 1H), 2.30-2.16 (m, 2H), 2.16-1.93 (m, 2H), 1.77 (t, J=9.8 Hz, 2H), 1.65-1.50 (m, 3H), 1.28 (s, 3H).

Selective Ester Reduction of IVa with LiBH$_4$: Hydroxy Amides VIIa

Starting amido-ester is dissolved in diethyl ether (0.1 M) under N$_2$ atmosphere and the solution is cooled to 0° C. with an ice bath. Then, a 2M solution of LiBH$_4$ in THF (1.5 eq.) is added dropwise and the mixture is stirred for 1 h, allowing it to reach room temperature.

At this time, a saturated aqueous solution of NH$_4$Cl is added carefully to quench the reaction, and the biphasic system is stirred for 30 min. Then, phases are separated and the aqueous layer is extracted three times with further EtOAc. After this, the whole organic phases are dried and evaporated under reduced pressure and the remaining oily crude is further purified with flash column chromatography in silica gel (hexanes/EtOAc 1:1) to yield the hydroxyl amides VIIa as colourless oils (yield: 82-87%).

According to this procedure, the following compounds VIIa were synthesized:

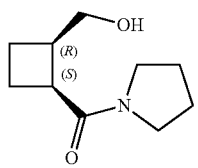

((1S,2R)-2-(Hydroxymethyl)cyclobutyl)(pyrrolidin-1-yl)methanone (yield: 87%)

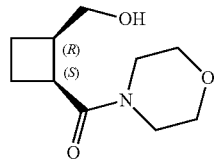

((1S,2R)-2-(Hydroxymethyl)cyclobutyl)(morpholino)methanone (yield: 82%)

Mitsunobu Reaction: Compounds VIa.

The procedure has been described above for examples 4-8 (yield: 52-81%). Accordingly, the following amidoethers VIa were synthesized:

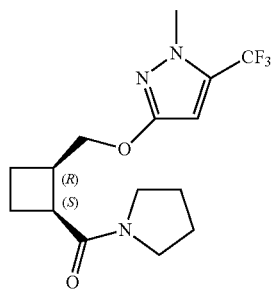

((1S,2R)-2-(((1-Methyl-5-(trifluoromethyl)-1H-pyrazol-3-yl)oxy)methyl)cyclobutyl) (pyrrolidin-1-yl)methanone (yield: 81%)

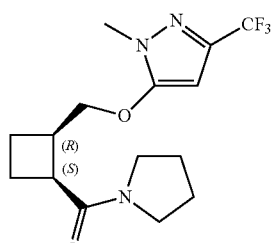

((1S,2R)-2-(((1-Methyl-5-(trifluoromethyl)-1H-pyrazol-3-yl)oxy)methyl)cyclobutyl) (morpholino)methanone (yield: 77%)

((1S,2R)-2-(((1-Methyl-3-(trifluoromethyl)-1H-pyrazol-5-yl)oxy)methyl)cyclobutyl) (pyrrolidin-1-yl)methanone (yield: 52%)

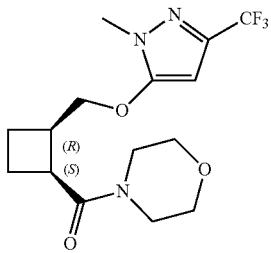

((1S,2R)-2-(((1-Methyl-3-(trifluoromethyl)-1H-pyrazol-5-yl)oxy)methyl)cyclobutyl) (morpholino)methanone (yield: 56%)

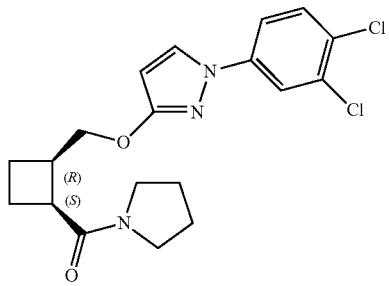

((1S,2R)-2-(((1-(3,4-Dichlorophenyl)-1H-pyrazol-3-yl)oxy)methyl)cyclobutyl) (pyrrolidin-1-yl)methanone (yield: 73%)

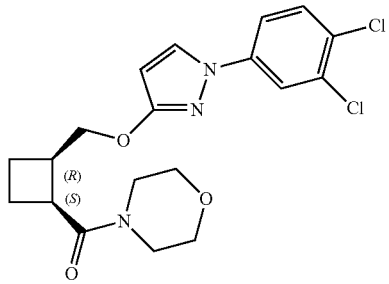

((1S,2R)-2-(((1-(3,4-Dichlorophenyl)-1H-pyrazol-3-yl)oxy)methyl)cyclobutyl) (morpholino)methanone (yield: 77%)

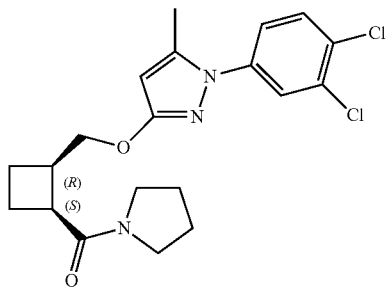

((1S,2R)-2-(((1-(3,4-Dichlorophenyl)-5-methyl-1H-pyrazol-3-yl)oxy)methyl)cyclobutyl)(pyrrolidin-1-yl)methanone (yield: 69%)

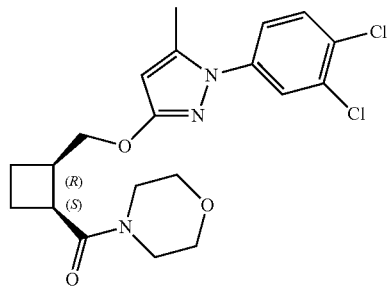

((1S,2R)-2-(((1-(3,4-Dichlorophenyl)-5-methyl-1H-pyrazol-3-yl)oxy)methyl)cyclobutyl)(morpholino)methanone (yield: 72%)

Reduction of VIa with LiAlH$_4$

Compounds of General Formula (Ia) (Examples 9-16)

Starting material is dissolved in THF (0.1 M) under N$_2$ atmosphere and the mixture is cooled to 0° C. with an ice bath. Then, LiAlH$_4$ (2.0 eq, 2.0 M in THF) is added dropwise to the solution and stirred for 30 minutes to 1 h. At 0° C., water (1 ml/g LiAlH$_4$) is added very slowly and stirred for 15 min. Then, a 10% solution of NaOH (2 ml/g LiAlH$_4$) is introduced and stirred for further 15 min. and finally, more water (3 ml/g LiAlH$_4$) is added. The resulting aluminium salts are filtered off by passing them through a pressed pad of Celite®, rinsing with EtOAc. Then, to the filtrate is added more water and the aqueous phase is extracted with EtOAc three times. The whole organic phases are dried and evaporated under reduced pressure to furnish the desired amino ethers Ia (Examples 9-16) as colourless oils (yield: 85-97%).

According to this procedure, the following compounds of general formula (Ia) were synthesized:

Example 9

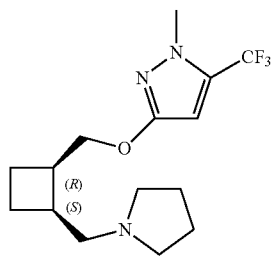

1-Methyl-3-(((1R,2S)-2-(pyrrolidin-1-ylmethyl)cyclobutyl)methoxy)-5-(trifluoromethyl)-1H-pyrazole (yield: 97%)

$^1$H NMR (360 MHz, CDCl$_3$) δ 5.97 (s, 1H), 4.28 (dd, J=9.9, 7.2 Hz, 1H), 4.15 (dd, J=10.0, 6.7 Hz, 1H), 3.80 (s, 3H), 2.79 (m, 2H), 2.71 (dd, J=12.7, 3.7 Hz, 1H), 2.50 (s br, 5H), 2.10 (m, 2H), 1.95-1.81 (m, 1H), 1.75 (s br, 5H).

Example 10

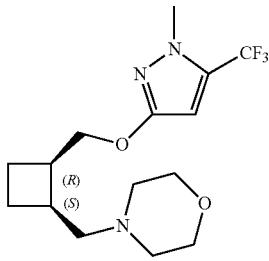

4-(((1S,2R)-2-(((1-Methyl-5-(trifluoromethyl)-1H-pyrazol-3-yl)oxy)methyl) cyclobutyl)methyl)morpholine (yield: 94%)

$^1$H NMR (360 MHz, CDCl$_3$) δ 5.97 (s, 1H), 4.22 (ddd, J=53.1, 9.9, 6.8 Hz, 2H), 3.81 (s, 3H), 3.73-3.58 (m, 4H), 2.87-2.66 (m, 2H), 2.59 (dd, J=12.3, 6.2 Hz, 1H), 2.48-2.27 (m, 5H), 2.19-1.98 (m, 2H), 1.92-1.65 (m, 2H).

Example 11

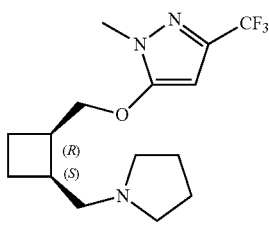

1-Methyl-5-(((1R,2S)-2-(pyrrolidin-1-ylmethyl)cyclobutyl)methoxy)-3-(trifluoromethyl)-1H-pyrazole (yield: 86%)

$^1$H NMR (360 MHz, CDCl$_3$) δ 5.74 (s, 1H), 4.24 (dd, J=9.5, 6.9 Hz, 1H), 4.09 (dd, J=9.4, 7.0 Hz, 1H), 3.64 (s, 3H), 2.87-2.60 (m, 3H), 2.40 (s br, 5H), 2.17-2.06 (m, 3H), 1.77-1.72 (m, 1H), 1.69 (s br, 4H).

Example 12

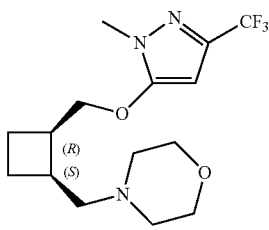

4-(((1S,2R)-2-(((1-Methyl-3-(trifluoromethyl)-1H-pyrazol-5-yl)oxy)methyl) cyclobutyl)methyl)morpholine (yields: 85%)

$^1$H NMR (360 MHz, CDCl$_3$) δ 5.82 (s, 1H), 4.38-4.09 (m, 4H), 3.76-3.60 (m, 5H), 3.38 (d, J=4.6 Hz, 1H), 3.06 (dd, J=12.7, 4.3 Hz, 1H), 2.90 (d, J=11.8 Hz, 3H), 2.79 (dd, J=12.6, 8.0 Hz, 1H), 2.67 (td, J=13.6, 3.1 Hz, 2H), 2.31-2.16 (m, 2H), 2.03 (s, 1H), 1.74 (s, 2H).

Example 13

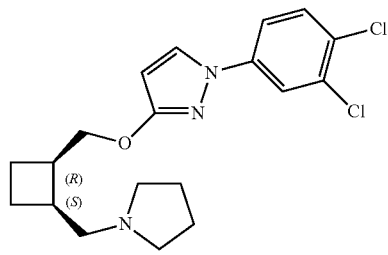

1-(3,4-Dichlorophenyl)-3-(((1R,2S)-2-(pyrrolidin-1-ylmethyl)cyclobutyl)methoxy)-1H-pyrazole (yield: 95%)

$^1$H NMR (360 MHz, MeOD-d$_4$) δ 7.73 (dd, J=25.4, 2.2 Hz, 2H), 7.52-7.37 (m, 2H), 5.92 (d, J=2.5 Hz, 1H), 4.37 (ddd, J=48.0, 10.1, 7.2 Hz, 2H), 2.99-2.70 (m, 3H), 2.65-2.46 (m, 5H), 2.14 (dt, J=6.5, 4.7 Hz, 2H), 1.93 (t, J=6.2 Hz, 1H), 1.78 (s, 5H).

Example 14

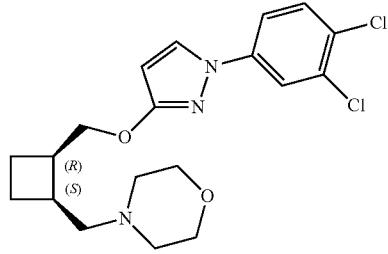

4-(((1S,2R)-2-(((1-(3,4-Dichlorophenyl)-1H-pyrazol-3-yl)oxy)methyl)cyclobutyl) methyl)morpholine (yield: 92%)

$^1$H NMR (360 MHz, CDCl$_3$) δ 8.09 (d, J=2.7 Hz, 1H), 7.89 (d, J=2.4 Hz, 1H), 7.59 (dt, J=20.4, 5.6 Hz, 2H), 5.98 (d, J=2.6 Hz, 1H), 4.47 (dd, J=10.3, 7.2 Hz, 1H), 4.31 (dd, J=10.3, 6.2 Hz, 1H), 3.72-3.59 (m, 4H), 2.93-2.68 (m, 3H), 2.50 (d, J=2.0 Hz, 4H), 2.25-2.04 (m, 2H), 1.98-1.76 (m, 2H).

Example 15

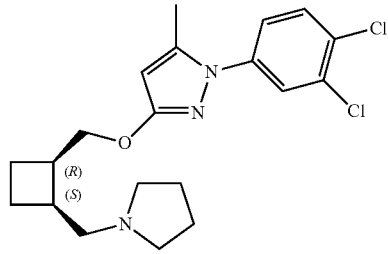

1-(3,4-Dichlorophenyl)-5-methyl-3-(((1R,2S)-2-(pyrrolidin-1-ylmethyl)cyclobutyl) methoxy)-1H-pyrazole (yield: 91%)

$^1$H NMR (360 MHz, CDCl$_3$) δ 7.58 (d, J=2.4 Hz, 1H), 7.47 (d, J=8.6 Hz, 1H), 7.28 (dd, J=8.5, 2.6 Hz, 1H), 5.65 (s,

1H), 4.34 (dd, J=10.1, 7.3 Hz, 1H), 4.20 (dd, J=10.1, 7.1 Hz, 1H), 2.88-2.64 (m, 3H), 2.54 (d, J=9.0 Hz, 1H), 2.47 (s br, 4H), 2.30 (s, 3H), 2.10 (td, J=7.7, 2.4 Hz, 2H), 1.95-1.81 (m, 1H), 1.73 (s br, 5H).

Example 16

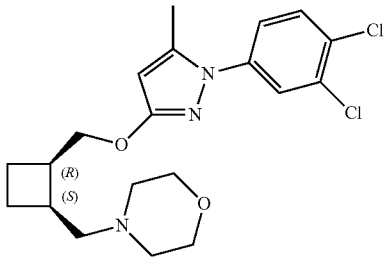

4-(((1S,2R)-2-(((1-(3,4-Dichlorophenyl)-5-methyl-1H-pyrazol-3-yl)oxy)methyl)cyclobutyl)methyl)morpholine (yield: 93%)

$^1$H NMR (360 MHz, CDCl$_3$) δ 7.58 (d, J=2.2 Hz, 1H), 7.48 (d, J=8.6 Hz, 1H), 7.28 (dd, J=9.6, 3.1 Hz, 1H), 5.66 (s, 1H), 4.36 (dd, J=9.9, 7.3 Hz, 1H), 4.20 (dd, J=9.9, 6.8 Hz, 1H), 3.67 (s br, 4H), 2.84-2.72 (m, 2H), 2.68-2.55 (m, 1H), 2.40 (s br, 5H), 2.31 (s, 3H), 2.14 (m, 2H), 1.79 (m, 2H).

General Procedure for the Formation of Hydrochlorides Ia.HCl (Examples 17-27)

Free amine derivative Ia is dissolved in diethyl ether (0.2 mM) and a 2N solution of HCl in diethyl ether is added (1.5 eq.), under N$_2$ atmosphere, and the mixture is stirred for 2 h. Then, the white solid is filtered and washed with more diethyl ether and pentane, and the white solid is dried under vacuum to afford the corresponding hydrochloride salts Ia.HCl as white solids (Examples 17-27) (yield: 60-98%.)

According to this procedure, the following salts Ia.HCl were synthesized:

Example 17

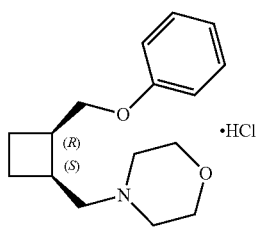

4-(((1S,2R)-2-(Phenoxymethyl)cyclobutyl)methyl)morpholine hydrochloride (yield: 89%)

$^1$H NMR (360 MHz, MeOD-d$_4$) δ 7.30 (dd, J=8.7, 7.4 Hz, 2H), 7.03-6.90 (m, 3H), 4.35-4.18 (m, 1H), 4.14-3.94 (m, 3H), 3.78 (d, J=11.9 Hz, 2H), 3.42 (dd, J=20.6, 15.2 Hz, 4H), 3.22-2.90 (m, 4H), 2.28 (dd, J=8.3, 5.0 Hz, 2H), 2.21-2.07 (m, 1H), 1.91-1.71 (m, 1H).

Example 18

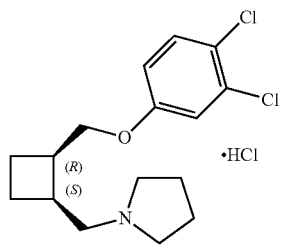

1-(((1S,2R)-2-((3,4-Dichlorophenoxy)methyl)cyclobutyl)methyl)pyrrolidine hydrochloride (yield: 87%)

$^1$H NMR (360 MHz, CDCl$_3$) δ 7.33 (d, J=8.0 Hz, 1H), 6.97 (s, 1H), 6.74 (d, J=6.4 Hz, 1H), 4.00 (s, 2H), 3.78 (s, 2H), 2.85 (s, 2H), 2.42 (s, 2H), 2.29 (s, 4H), 2.18 (s, 6H), 1.90 (s, 2H).

Example 19

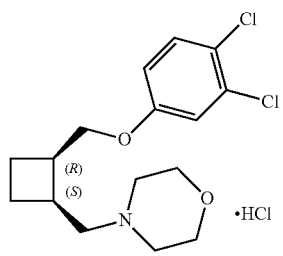

4-(((1S,2R)-2-((3,4-Dichlorophenoxy)methyl)cyclobutyl)methyl)morpholine hydrochloride (yield: 91%)

$^1$H NMR (360 MHz, MeOD-d$_4$) δ 7.39 (d, J=8.8 Hz, 1H), 7.13 (d, J=10.4 Hz, 1H), 6.90 (t, J=7.8 Hz, 1H), 4.37-3.99 (m, 3H), 3.71 (s, 3H), 3.37 (s, 1H), 3.08 (d, J=12.9 Hz, 1H), 2.93-2.60 (m, 6H), 2.18 (s, 2H), 1.88 (d, J=55.2 Hz, 1H), 1.73 (s, 1H).

Example 20

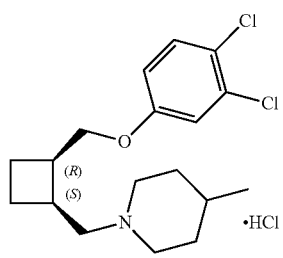

1-(((1S,2R)-2-((3,4-Dichlorophenoxy)methyl)cyclobutyl)methyl)-4-methylpiperidine hydrochloride (yield: 79%)

$^1$H NMR (360 MHz, CDCl$_3$) δ 7.37 (d, J=8.8 Hz, 1H), 7.03 (d, J=2.4 Hz, 1H), 6.79 (dd, J=8.8, 2.4 Hz, 1H), 4.21-3.99 (m, 2H), 3.48 (dd, J=17.8, 10.9 Hz, 3H), 3.25 (d, J=12.6 Hz, 1H), 2.98 (s, 2H), 2.59 (dd, J=26.2, 11.3 Hz, 2H), 2.42-1.90 (m, 7H), 1.79 (d, J=12.2 Hz, 3H), 1.59 (s, 1H), 1.05 (d, J=6.4 Hz, 3H).

Example 21

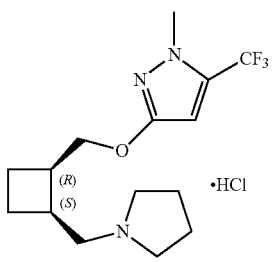

1-Methyl-3-(((1R,2S)-2-(pyrrolidin-1-ylmethyl)cyclobutyl)methoxy)-5-(trifluoromethyl)-1H-pyrazole hydrochloride (yield: 98%)

¹H NMR (360 MHz, MeOD-d₄) δ 6.24 (s, 1H), 4.37 (dd, J=10.3, 9.0 Hz, 1H), 4.24 (dd, J=10.4, 4.8 Hz, 1H), 3.83 (s, 3H), 3.62 (m, 2H), 3.43 (dd, J=12.8, 5.3 Hz, 1H), 3.35 (d, J=8.5 Hz, 1H), 3.06 (dd, J=17.1, 9.0 Hz, 2H), 2.94 (dd, 2H), 2.23 (t, J=8.2 Hz, 2H), 2.17-1.95 (m, 5H), 1.73 (t, J=11.7 Hz, 1H).

Example 22

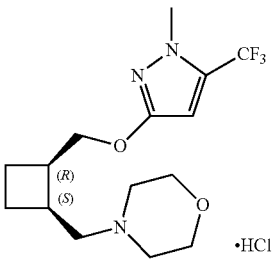

4-(((1S,2R)-2-(((1-Methyl-5-(trifluoromethyl)-1H-pyrazol-3-yl)oxy)methyl)cyclo butyl)methyl)morpholine hydrochloride (yield: 96%)

¹H NMR (360 MHz, MeOD-d₄) δ 6.25 (s, 1H), 4.32 (ddd, J=15.6, 10.6, 7.1 Hz, 2H), 4.03 (d, J=12.8 Hz, 2H), 3.83 (s, 5H), 3.43 (dd, J=13.1, 5.6 Hz, 3H), 3.15 (t, J=11.7 Hz, 2H), 3.09-3.00 (m, 1H), 2.97 (dd, J=7.8, 3.9 Hz, 1H), 2.33-2.19 (m, 2H), 2.19-2.06 (m, 1H), 1.75 (dd, J=14.2, 6.7 Hz, 1H).

Example 23

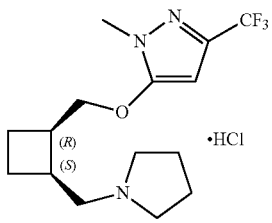

1-Methyl-5-(((1R,2S)-2-(pyrrolidin-1-ylmethyl)cyclobutyl)methoxy)-3-(trifluoro methyl)-1H-pyrazole hydrochloride (yield: 60%)

¹H NMR (360 MHz, MeOD-d₄) δ 6.12 (s, 1H), 4.47-4.35 (m, 1H), 4.27 (dd, J=9.5, 5.3 Hz, 1H), 3.92-3.75 (m, 2H), 3.70 (s, 3H), 3.64 (s br, 3H), 3.45 (d, J=6.4 Hz, 2H), 3.05 (m, 5H), 2.33-1.96 (m, 8H), 1.83 (m, 1H).

Example 24

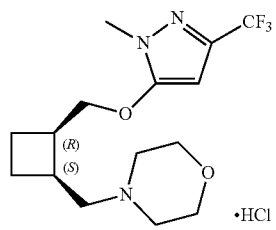

4-(((1S,2R)-2-(((1-Methyl-3-(trifluoromethyl)-1H-pyrazol-5-yl)oxy)methyl)cyclobutyl)methyl)morpholine hydrochloride (yield: 67%)

¹H NMR (360 MHz, MeOD-d₄) δ 6.10 (d, J=8.5 Hz, 1H), 4.39 (dd, J=32.3, 24.2 Hz, 2H), 4.09-3.91 (m, 2H), 3.80 (dd, J=11.4, 8.3 Hz, 2H), 3.70 (s, 4H), 3.50-3.41 (m, 3H), 3.25-3.05 (m, 3H), 2.90 (dd, J=8.1, 3.8 Hz, 2H), 2.37-2.06 (m, 3H), 1.81 (d, J=38.5 Hz, 1H).

Example 25

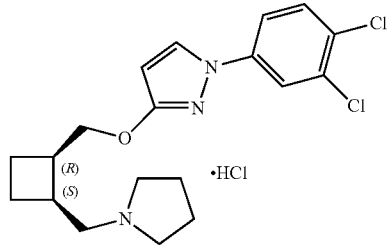

1-(3,4-Dichlorophenyl)-3-(((1R,2S)-2-(pyrrolidin-1-ylmethyl)cyclobutyl)methoxy)-1H-pyrazole hydrochloride (yield: 85%)

¹H NMR (360 MHz, MeOD-d₄) δ 8.15 (d, J=2.6 Hz, 1H), 7.93 (d, J=2.3 Hz, 1H), 7.63 (dt, J=19.3, 5.6 Hz, 2H), 6.07 (d, J=2.6 Hz, 1H), 4.60-4.27 (m, 2H), 3.65 (s, 2H), 3.57-3.36 (m, 2H), 3.05 (d, J=33.4 Hz, 4H), 2.40-2.22 (m, 2H), 2.13 (dd, J=24.7, 18.0 Hz, 5H), 1.82 (d, J=10.2 Hz, 1H).

Example 26

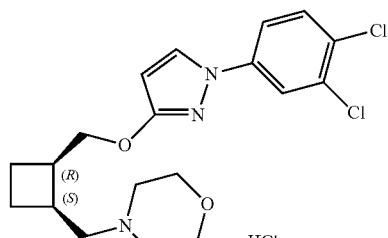

4-(((1S,2R)-2-(((1-(3,4-Dichlorophenyl)-1H-pyrazol-3-yl)oxy)methyl)cyclobutyl) methyl)morpholine hydrochloride (yield: 92%)

$^1$H NMR (360 MHz, MeOD-d$_4$) δ 8.15 (d, J=2.4 Hz, 1H), 7.91 (d, J=2.2 Hz, 1H), 7.62 (dt, J=20.8, 5.5 Hz, 2H), 6.07 (d, J=2.4 Hz, 1H), 4.55-4.33 (m, 2H), 4.04 (d, J=13.1 Hz, 2H), 3.85 (dd, J=20.3, 11.9 Hz, 2H), 3.47 (d, J=12.6 Hz, 3H), 3.39 (d, J=8.3 Hz, 1H), 3.24-2.94 (m, 4H), 2.37-2.10 (m, 3H), 1.81 (t, J=9.9 Hz, 1H).

Example 27

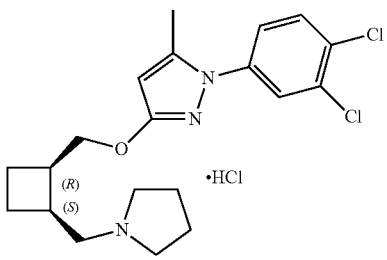

1-(3,4-Dichlorophenyl)-5-methyl-3-(((1R,2S)-2-(pyrrolidin-1-ylmethyl)cyclobutyl)methoxy)-1H-pyrazole hydrochloride (yield: 88%)

$^1$H NMR (360 MHz, MeOD-d$_4$) δ 7.71 (d, J=2.3 Hz, 1H), 7.66 (d, J=8.7 Hz, 1H), 7.45 (dd, J=8.6, 2.3 Hz, 1H), 5.90 (s, 1H), 4.47-4.35 (m, 1H), 4.28 (dd, J=10.5, 5.2 Hz, 1H), 3.74-3.55 (m, 2H), 3.47 (dd, J=12.7, 5.6 Hz, 1H), 3.41-3.34 (m, 1H), 3.17-2.86 (m, 4H), 2.35 (s, 3H), 2.23 (m, 2H), 2.14 (m, 3H), 2.08-1.96 (m, 2H), 1.77 (m, 1H).

Synthesis of (R,R)-Stereoisomers

Compounds of General Formula (Ib) According to the Synthetic Pathway Disclosed in Scheme No 2

Epimerization of Cis-Amides VIa: Trans-Amides VIb
Method A: KHMDS as a Base

The starting material is dissolved in THF under nitrogen atmosphere and once the system is cooled to 0° C. a solution of potassium hexamethyldisilazide (0.5 M in toluene, 1.5 eq.) is added dropwise. Immediately, the cooling bath is removed and the mixture is stirred at room temperature for 1 h.

Water is added to quench the reaction along with dichloromethane (several). The organic phase is then washed with more water and brine, affording a yellowish oil that consists in a mixture cis/trans 10/90. In order to separate both diastereoisomers, a flash column chromatography in silica gel (hexanes/EtOAc 2:1) is carried out, obtaining the desired trans diastereoisomers VIb as colourless oils (yield: 80-85%).

Accordingly, the following compounds VIb were synthesized:

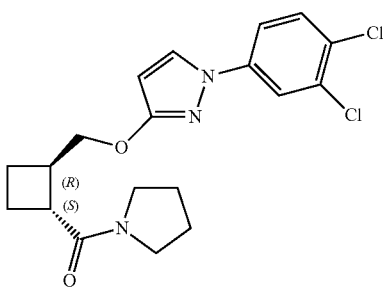

((1R,2R)-2-(((1-(3,4-Dichlorophenyl)-1H-pyrazol-3-yl)oxy)methyl)cyclobutyl)(pyrrolidin-1-yl)methanone (yield: 80%)

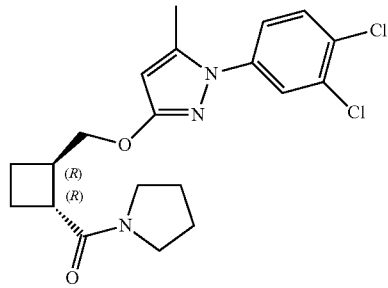

((1R,2R)-2-(((1-(3,4-Dichlorophenyl)-5-methyl-1H-pyrazol-3-yl)oxy)methyl)cyclobutyl)(pyrrolidin-1-yl)methanone (yield: 85%)

Method B: KO$^t$Bu/$^t$BuOH as a Base

The corresponding amido-ether is dissolved in tert-butanol (0.05 M) and four equivalents of KO$^t$Bu are added. The reaction system is heated to 100° C. and stirred for 5 hours, observing no presence of starting material in TLC.

A little bit of water is added and volatiles are removed under reduced pressure. The oily crude is then partitioned between water and EtOAc and the phases are separated. The organic phase is dried and evaporated under vacuum affording a yellowish oil that consists in a mixture cis/trans 10/90. In order to separate both diastereoisomers, a flash column chromatography in silica gel (hexanes/EtOAc 2:1) is carried out, obtaining the desired trans diastereoisomer VIb as a colourless oil (yield: 62%).

Accordingly, the following compound VIb was synthesized:

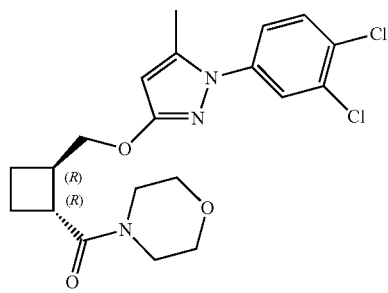

((1R,2R)-2-(((1-(3,4-Dichlorophenyl)-5-methyl-1H-pyrazol-3-yl)oxy)methyl)cyclobutyl)(morpholino)methanone (yield: 62%)

Reduction of Amides VIb to Compounds of General Formula (Ib) (Examples 28-30)

Reduction was achieved following the same procedure as described for examples 9-16 to afford amino ethers Ib as colourless oils (Examples 28-30).

According to this procedure, the following compounds of general formula (Ib) were synthesized:

Example 28

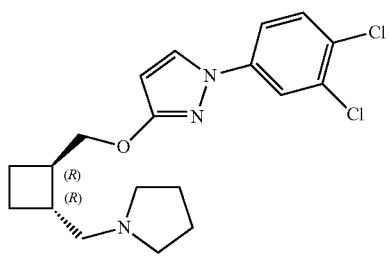

1-(3,4-Dichlorophenyl)-3-(1R,2R)-2-(pyrrolidin-1-ylmethyl)cyclobutyl)methoxy)-1H-pyrazole (yield: 87%)

$^1$H NMR (360 MHz, CDCl$_3$) δ 7.75 (d, J=2.1 Hz, 1H), 7.68 (d, J=2.5 Hz, 1H), 7.49-7.38 (m, 2H), 5.92 (d, J=2.5 Hz, 1H), 4.22 (d, J=3.8 Hz, 2H), 2.73 (d, J=6.8 Hz, 1H), 2.56-2.36 (m, 7H), 2.18-1.97 (m, 2H), 1.89-1.61 (m, 6H).

Example 29

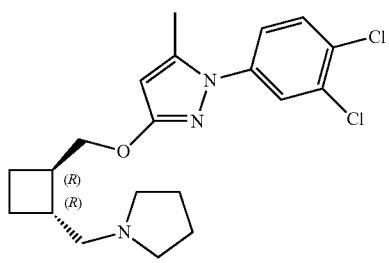

1-(3,4-Dichlorophenyl)-5-methyl-3-(((1R,2R)-2-(pyrrolidin-1-ylmethyl)cyclobutyl) methoxy)-1H-pyrazole (yield: 94%)

$^1$H NMR (360 MHz, CDCl$_3$) δ 7.58 (d, J=2.5 Hz, 1H), 7.47 (d, J=8.6 Hz, 1H), 7.28 (dd, J=8.7, 2.5 Hz, 1H), 5.66 (s, 1H), 4.14 (dd, J=5.7, 2.2 Hz, 2H), 2.70 (d, J=8.9 Hz, 1H), 2.48 (s br, 4H), 2.43-2.35 (m, 2H), 2.30 (s, 3H), 2.09 (m, 1H), 2.05-1.92 (m, 1H), 1.75 (s br, 5H), 1.70-1.58 (m, 1H).

Example 30

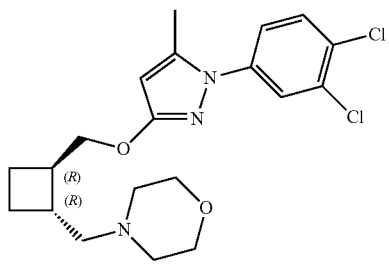

4-(((1R,2R)-2-(((1-(3,4-Dichlorophenyl)-5-methyl-1H-pyrazol-3-yl)oxy)methyl)cyclobutyl)methyl)morpholine (yield: 82%)

$^1$H NMR (360 MHz, CDCl$_3$) δ 7.57 (d, J=2.4 Hz, 1H), 7.47 (d, J=8.6 Hz, 1H), 7.31-7.24 (dd, J=8.6, 2.4 Hz, 1H), 5.65 (s, 1H), 4.13 (d, J=5.7 Hz, 2H), 3.68 (t, J=4.6 Hz, 4H), 2.56 (dd, J=11.2, 4.5 Hz, 1H), 2.49-2.33 (m, 6H), 2.30 (s, 3H), 2.14-1.93 (m, 2H), 1.87-1.72 (m, 1H), 1.72-1.55 (m, 1H).

Epimerization of Cis-Amides IVc: Trans-Amides IVb.

Starting material IVc is dissolved in $^i$PrOH (0.05 M) and sodium methoxide (10 eq.) is added at room temperature, all in one portion. After 2 h., a TLC analysis shows totally conversion of the product as a carboxylate, due to saponification carried out after epimerization.

The solution is acidified to pH=2 with a 2N solution of HCl, and dichloromethane is added. Then, the phases are separated, and the aqueous is washed with more dichloromethane. The whole organic layers are dried and evaporated under reduced pressure, affording trans-carboxylic acid as colourless oil, which is used in the next step without further purification.

The crude obtained in the first step is dissolved in methanol (0.1 M), and sulfuric acid (1.1 eq.) is added dropwise. The reaction mixture is stirred at room temperature overnight.

Volatiles are removed under vacuum and dichloromethane is added. The organic layer is washed with water (slightly basic) and brine, dried and evaporated under reduced pressure to afford the desired trans amido-ester IVb as a colourless oil. (yield: 90%).

Accordingly, the following compound IVb was synthesized:

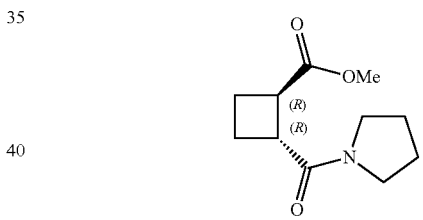

(1R,2R)-Methyl 2-(pyrrolidine-1-carbonyl)cyclobutanecarboxylate (yield: 90%)

Reduction of Amides IVb: Alcohols VIIb.

Reduction was achieved as described above for compounds IVa, affording alcohols VIIb as a colourless oils. (yield: 84%)

Accordingly, the following compound VIIb was synthesized:

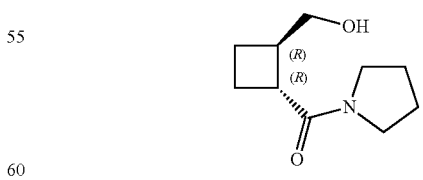

((1R,2R)-2-(Hydroxymethyl)cyclobutyl)(pyrrolidin-1-yl)methanone (yield: 84%)

Mitsunobu Reaction of Alcohols VIIb: Compounds VIb.

This reaction was carried out as described above for compounds VIa affording the amido ether VIb as a colourless oil. (yield: 68%)

According to this procedure, the following compound VIb was synthesized:

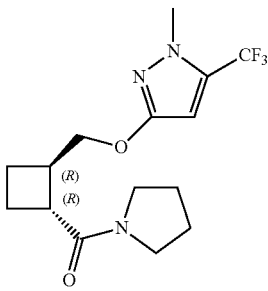

(((1R,2R)-2-(((1-Methyl-5-(trifluoromethyl)-1H-pyrazol-3-yl)oxy)methyl)cyclobutyl) (pyrrolidin-1-yl)methanone (yield: 68%)

Reduction of VIb

Compounds of General Formula (Ib) (Example 31) and their Hydrochloride Salts (Example 32)

This reaction was carried out as described above for examples 9-16, affording Ib as a colourless oil (Example 31) which was transformed into its hydrochloride salt Ib.HCl (Example 32), obtained as a white solid, following the same procedure described for examples 17-27.

Accordingly, compound Ib and its salt Ib.HCl were synthesized:

Example 31

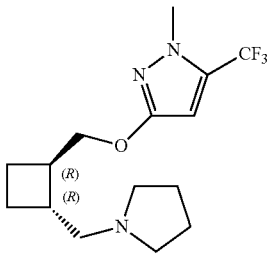

1-Methyl-3-(((1R,2R)-2-(pyrrolidin-1-ylmethyl)cyclobutyl)methoxy)-5-(trifluoromethyl)-1H-pyrazole (yield: 96%)
$^1$H NMR (250 MHz, CDCl$_3$) δ 5.98 (s, 1H), 4.10 (d, J=7.1 Hz, 2H), 3.81 (s, 3H), 2.99-2.35 (m, 8H), 2.21-1.69 (m, 8H).

Example 32

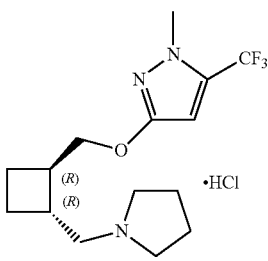

1-Methyl-3-(((1R,2R)-2-(pyrrolidin-1-ylmethyl)cyclobutyl)methoxy)-5-(trifluoro methyl)-1H-pyrazole hydrochloride (yield: 90%)
$^1$H NMR (250 MHz, MeOD-d$_4$) δ 6.20 (s, 1H), 4.15 (qd, J=10.3, 5.8 Hz, 2H), 3.82 (s, 3H), 3.74-3.55 (m, 2H), 3.50-3.21 (m, 2H), 3.16-2.97 (m, 2H), 2.63 (dt, J=15.1, 8.3 Hz, 2H), 2.29-1.79 (m, 8H).

Synthesis of Amides IVc

According to Synthetic Pathway Described in Scheme 3

Synthesis of Amido Esters VIII

Free carboxylic acid IX, prepared according to the methods previously described in S. Izquierdo, F. Rúa, A. Sbai. T. Parella, Á. Álvarez-Larena, V. Branchadell, R. M. Ortuño, J. Org. Chem. 2005, 70, 7963-7971, is dissolved in dichloromethane (0.05 M) and PyBOP (1.5 eq.) and DIPEA (2 eq.) are added. After stirring for 10 minutes, pyrrolidine (2 eq.) is added and the system allowed to stir for 24 h. At this time, the solvent is removed in vacuo and the crude oil is purified by flash column chromatography through Celite® in silica gel (hexanes/EtOAc 2:1) to afford the corresponding amido esters VIII as yellowish oils. (yield: 85-99%).

According to this procedure, the following compounds VIII were synthesized:

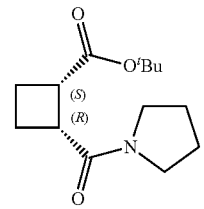

(1S,2R)-tert-Butyl 2-(pyrrolidine-1-carbonyl)cyclobutanecarboxylate (yield: 99%)

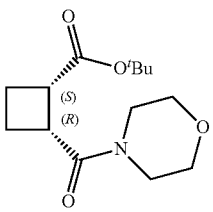

(1S,2R)-tert-Butyl 2-(morpholine-4-carbonyl)cyclobutanecarboxylate (yield: 85%)

Synthesis of Amido Esters IVc

Starting amido-ester VIII is dissolved in TFA/DCM (1/1, 0.05 M). After 1 h stirring at room temperature, the solvent is removed and the residue taken up in toluene and evaporated again to yield the free carboxylic acid as colourless oil. (yield: quantitative)

The crude obtained in the first step is dissolved in methanol (0.1 M), and sulfuric acid (1.1 eq.) is added dropwise. The reaction mixture is stirred at room temperature overnight. Volatiles are removed under vacuum and dichloromethane is added. The organic layer is washed with water (slightly basic) and brine, dried and evaporated under reduced pressure to afford the desired amide methyl esters IVc as colourless oils. (yield: 99%).

According to this procedure, the following compounds IVc were synthesized:

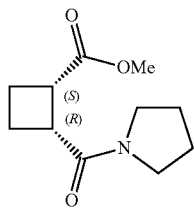

(1S,2R)-Methyl 2-(pyrrolidine-1-carbonyl)cyclobutanecarboxylate (yield: 99%)

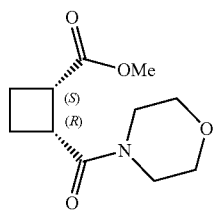

(1S,2R)-Methyl 2-(morpholine-4-carbonyl)cyclobutanecarboxylate (yield: 99%)

Synthesis of (S,R)-Stereoisomers

Compounds of General Formula (Ic) According to the Synthetic Pathway Disclosed in Scheme No 4

All procedures are similar to those already described for the preparation of enantiomeric compounds of general formula (Ia).

Accordingly, hydroxy amides VIIc, ethers VIc and compounds of general formula (Ic) (Example 33) as well as its hydrochloride salt Ic.HCl (Example 34) were synthesized.

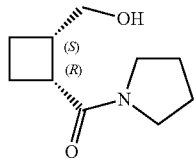

((1R,2S)-2-(Hydroxymethyl)cyclobutyl)(pyrrolidin-1-yl)methanone (yield: 83%)

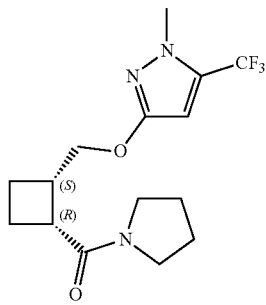

((1R,2S)-2-(((1-Methyl-5-(trifluoromethyl)-1H-pyrazol-3-yl)oxy)methyl)cyclobutyl) (pyrrolidin-1-yl)methanone (yield: 72%)

Example 33

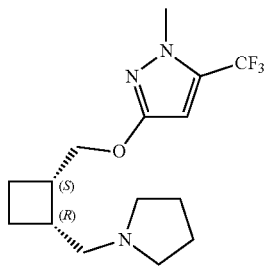

1-Methyl-3-(((1S,2R)-2-(pyrrolidin-1-ylmethyl)cyclobutyl)methoxy)-5-(trifluoromethyl)-1H-pyrazole (yield: 94%)
$^1$H NMR (360 MHz, CDCl$_3$) δ 5.97 (s, 1H), 4.28 (dd, J=9.9, 7.2 Hz, 1H), 4.15 (dd, J=10.0, 6.7 Hz, 1H), 3.80 (s, 3H), 2.79 (m, 2H), 2.71 (dd, J=12.7, 3.7 Hz, 1H), 2.50 (s br, 5H), 2.10 (m, 2H), 1.95-1.81 (m, 1H), 1.75 (s br, 5H).

Example 34

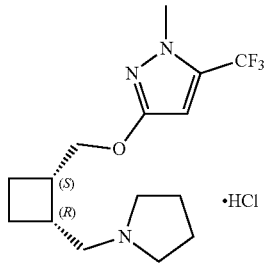

1-Methyl-3-(((1S,2R)-2-(pyrrolidin-1-ylmethyl)cyclobutyl)methoxy)-5-(trifluoro methyl)-1H-pyrazole hydrochloride (yield: 89%)
$^1$H NMR (360 MHz, MeOD-d$_4$) δ 6.24 (s, 1H), 4.37 (dd, J=10.3, 9.0 Hz, 1H), 4.24 (dd, J=10.4, 4.8 Hz, 1H), 3.83 (s, 3H), 3.62 (m, 2H), 3.43 (dd, J=12.8, 5.3 Hz, 1H), 3.35 (d, J=8.5 Hz, 1H), 3.06 (dd, J=17.1, 9.0 Hz, 2H), 2.94 (dd, 2H), 2.23 (t, J=8.2 Hz, 2H), 2.17-1.95 (m, 5H), 1.73 (t, J=11.7 Hz, 1H).

Synthesis of (S,S)-Stereoisomers: Compounds of General Formula (Id) According to the Synthetic Pathway Disclosed in Scheme No 5

Epimerization of Cis-Ester IVa: Synthesis of Trans-Ester IVd.

Starting material IVa is dissolved in $^i$PrOH (0.05 M), and sodium methoxide (10 eq.) is added at room temperature, all in one portion. After 2 h., a TLC analysis shows totally conversion of the product to a carboxylate, due to saponification carried out after epimerization.

The solution is acidified to pH=2 with a 2N solution of HCl, and several dichloromethane is added. Then, the phases are separated, and the aqueous is washed with more dichloromethane. The whole organic layers are dried and evaporated under reduced pressure, affording trans-carboxylic acid as colourless oil, which is used in the next step without further purification.

The crude obtained in the first step is dissolved in methanol (0.1 M), and sulfuric acid (1.1 eq.) is added dropwise. The reaction mixture is stirred at room temperature overnight.

Volatiles are removed under vacuum and dichloromethane is added. The organic layer is washed with water (slightly basic) and brine, dried and evaporated under reduced pressure to afford the desired trans amido-esters IVd as colourless oils. (yield: 84-95%)

Accordingly, the following compounds IVd were synthesized:

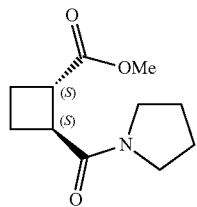

(1S,2S)-Methyl 2-(pyrrolidine-1-carbonyl)cyclobutanecarboxylate (yield: 95%)

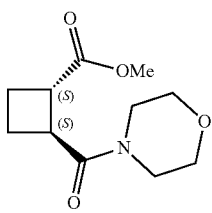

(1S,2S)-Methyl 2-(morpholine-4-carbonyl)cyclobutanecarboxylate (yield: 84%)

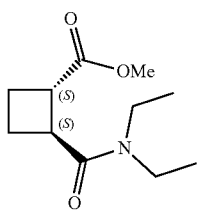

(1S,2S)-Methyl 2-(diethylcarbamoyl)cyclobutanecarboxylate (yield: 86%)

Selective reduction of the ester group in IVd was achieved as described above for compounds VIa, affording hydroxy amides VIId.

Accordingly, the following hydroxyl amides VIId were synthesized:

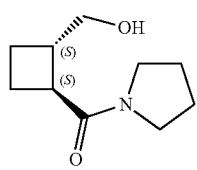

((1S,2S)-2-(Hydroxymethyl)cyclobutyl)(pyrrolidin-1-yl)methanone (yield: 86%)

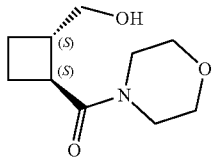

((1S,2S)-2-(Hydroxymethyl)cyclobutyl)(morpholino)methanone (yield: 83%)

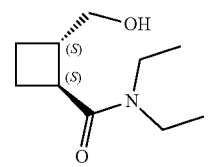

(1S,2S)—N,N-Diethyl-2-(hydroxymethyl)cyclobutanecarboxamide (yield: 84%)

Mitsunobu reaction of these alcohols with phenols $R^1OH$ was carried out following the same procedure described above for compounds VIa, producing amido ethers VId as colourless oils.

According to this procedure, the following amido ethers VId were synthesized:

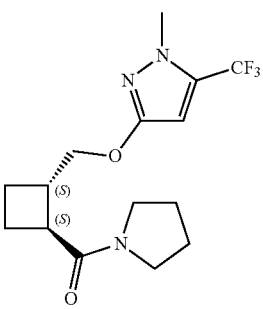

((1S,2S)-2-(((1-Methyl-5-(trifluoromethyl)-1H-pyrazol-3-yl)oxy)methyl)cyclobutyl) (pyrrolidin-1-yl)methanone (yield: 74%)

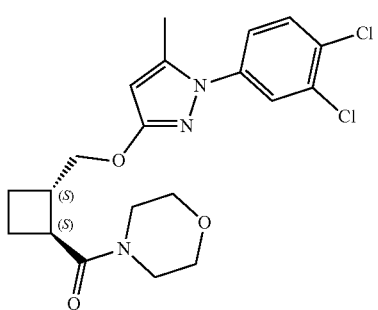

(((1S,2S)-2-(((1-(3,4-Dichlorophenyl)-5-methyl-1H-pyrazol-3-yl)oxy)methyl)cyclobutyl)(morpholino)methanone (yield: 69%)

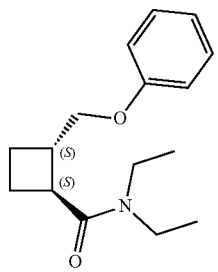

(1S,2S)—N,N-Diethyl-2-(phenoxymethyl)cyclobutanecarboxamide (yield: 78%)

Finally, reduction of amides VId with LiAlH₄ as described above for examples 9-16, allowed us to obtain compounds of general formula (Id) (Examples 35-37) as colourless oils. Hydrochloride salts Id.HCl (Examples 38 and 39) were also prepared as white solids, using the same procedure performed for examples 17-27.

Accordingly, the following compounds of general formula (Id) and their hydrochloride salt Id.HCl were synthesized:

Example 35

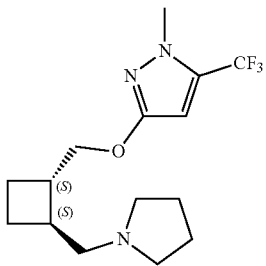

1-Methyl-3-(((1S,2S)-2-(pyrrolidin-1-ylmethyl)cyclobutyl)methoxy)-5-(trifluoro methyl)-1H-pyrazole (yield: 90%)
¹H NMR (250 MHz, CDCl₃) δ 5.98 (s, 1H), 4.10 (d, J=7.1 Hz, 2H), 3.81 (s, 3H), 2.99-2.35 (m, 8H), 2.21-1.69 (m, 8H).

Example 36

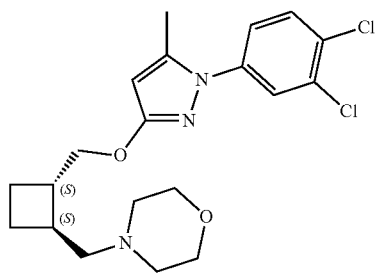

4-(((1S,2S)-2-(((1-(3,4-Dichlorophenyl)-5-methyl-1H-pyrazol-3-yl)oxy)methyl)cyclobutyl)methyl)morpholine (yield: 86%)
¹H NMR (360 MHz, CDCl₃) δ 7.57 (d, J=2.4 Hz, 1H), 7.47 (d, J=8.6 Hz, 1H), 7.31-7.24 (dd, J=8.6, 2.4 Hz, 1H), 5.65 (s, 1H), 4.13 (d, J=5.7 Hz, 2H), 3.68 (t, J=4.6 Hz, 4H), 2.56 (dd, J=11.2, 4.5 Hz, 1H), 2.49-2.33 (m, 6H), 2.30 (s, 3H), 2.14-1.93 (m, 2H), 1.87-1.72 (m, 1H), 1.72-1.55 (m, 1H).

Example 37

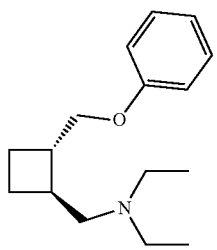 [SMILES: CCN(CC)C[C@H]1CC[C@@H]1COc1ccccc1]

N,N-Diethyl-N-(((1S,2S)-2-(phenoxymethyl)cyclobutyl)methyl)ethanamine (yield: 81%)
¹H NMR (250 MHz, CDCl₃) δ 7.33-7.21 (m, 2H), 6.90 (dd, J=7.7, 6.6 Hz, 3H), 3.94 (d, J=3.7 Hz, 2H), 2.71 (dd, J=11.2, 6.4 Hz, 1H), 2.57 (dd, J=14.0, 7.0 Hz, 5H), 2.40 (dd, J=13.6, 6.5 Hz, 2H), 2.20-1.97 (m, 4H), 1.74 (dd, J=26.2, 10.4 Hz, 2H), 1.04 (d, J=7.2 Hz, 6H).

Example 38

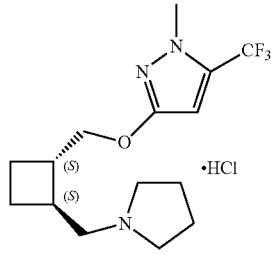

1-Methyl-3-(((1S,2S)-2-(pyrrolidin-1-ylmethyl)cyclobutyl)methoxy)-5-(trifluoromethyl)-1H-pyrazole hydrochloride (yield: 92%)
¹H NMR (250 MHz, MeOD-d₄) δ 6.20 (s, 1H), 4.15 (qd, J=10.3, 5.8 Hz, 2H), 3.82 (s, 3H), 3.74-3.55 (m, 2H), 3.50-3.21 (m, 2H), 3.16-2.97 (m, 2H), 2.63 (dt, J=15.1, 8.3 Hz, 2H), 2.29-1.79 (m, 8H).

Example 39

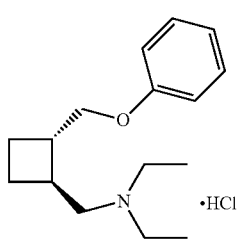 [SMILES: CCN(CC)C[C@H]1CC[C@@H]1COc1ccccc1 ; Cl]

N,N-Diethyl-N-(((1S,2S)-2-(phenoxymethyl)cyclobutyl)methyl)ethanamine hydrochloride (yield: 78%)

$^1$H NMR (250 MHz, CDCl$_3$) δ 7.38-7.22 (m, 2H), 6.96 (dd, J=8.1, 3.2 Hz, 3H), 4.03 (qd, J=9.6, 5.9 Hz, 2H), 3.43-3.36 (m, 1H), 3.23 (q, J=7.3 Hz, 5H), 2.78-2.55 (m, 2H), 2.26 (m, 1H), 2.19-2.04 (m, 1H), 1.93 (m, 2H), 1.34 (t, J=7.3 Hz, 6H).

Particular compounds of general formula (I) are listed in table (I) below.

TABLE I

| STRUCTURE | Example No | NAME | NMR |
|---|---|---|---|
| 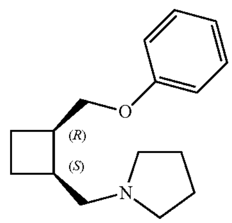 | 1 | 1-(((1S,2R)-2-(phenoxymethyl)cyclobutyl)methyl)pyrrolidine | $^1$H NMR (360 MHz, CDCl$_3$) δ 7.30 (m, 2H), 6.94 (m, 3H), 4.04 (t, J = 7.0 Hz, 2H), 2.86 (d, J = 10.0 Hz, 2H), 2.77 (m, 2H), 2.55 (t, J = 7.5 Hz, 2H), 2.14 (m, 2H), 2.03 (m, 2H), 1.91 (m, 2H), 1.76 (m, 4H). |
| 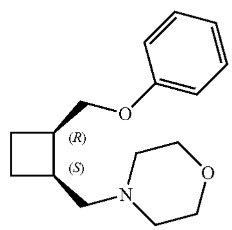 | 2 | 4-(((1S,2R)-2-(phenoxymethyl)cyclobutyl)methyl)morpholine | $^1$H NMR (360 MHz, CDCl$_3$) δ 7.28 (dd, J = 8.6, 7.5 Hz, 2H), 6.99-6.82 (m, 3H), 4.16 (dd, J = 9.3, 6.8 Hz, 1H), 4.01 (dd, J = 9.4, 6.4 Hz, 1H), 3.67 (t, J = 4.7 Hz, 4H), 2.81 (dd, J = 5.1, 2.9 Hz, 2H), 2.64 (dd, J = 12.3, 6.4 Hz, 1H), 2.52-2.29 (m, 4H), 2.24-2.02 (m, 2H), 1.82 (dd, J = 8.6, 3.8 Hz, 2H). |
| 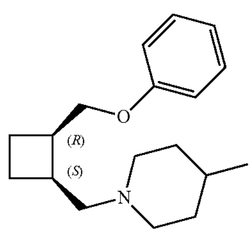 | 3 | 4-methyl-1-(((1S,2R)-2-(phenoxymethyl)cyclobutyl)methyl)piperidine | $^1$H NMR (360 MHz, CDCl$_3$) δ 7.30 (m, 2H), 6.94 (m, 3H), 4.19 (dd, J = 9.0, 6.0 Hz, 1H), 4.03 (dd, J = 9.0, 6.0 Hz, 1H), 2.82 (m, 4H), 2.63 (dd, J = 12.0, 6.0 Hz, 1H), 2.14 (m, 2H), 1.91 (m, 4H), 1.61 (m, 2H), 1.26 (m, 3H), 0.92 (d, J = 6.0 Hz, 3H). |
| 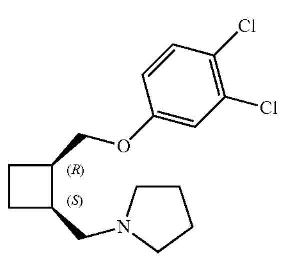 | 4 | 1-(((1S,2R)-2-((3,4-dichlorophenoxy)methyl)cyclobutyl)methyl)pyrrolidine | $^1$H NMR (360 MHz, CDCl$_3$) δ 7.32 (d, J = 8.8 Hz, 1H), 7.00 (s, 1H), 6.76 (d, J = 8.8 Hz, 1H), 3.99 (t, J = 6.2 Hz, 2H), 2.90 (d, J = 9.3 Hz, 2H), 2.79 (s, 2H), 2.57 (t, J = 7.3 Hz, 2H), 2.23-2.03 (m, 4H), 1.88 (dt, J = 12.7, 6.4 Hz, 2H), 1.75 (s, 4H). |
| 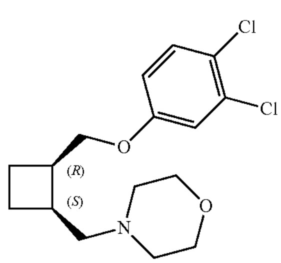 | 5 | 4-(((1S,2R)-2-((3,4-dichlorophenoxy)methyl)cyclobutyl)methyl)morpholine | $^1$H NMR (360 MHz, CDCl$_3$) δ 7.34 (d, J = 8.9 Hz, 1H), 7.02 (d, J = 2.8 Hz, 1H), 6.78 (dd, J = 8.9, 2.9 Hz, 1H), 4.31-4.02 (m, 4H), 3.74-3.60 (m, 2H), 3.37 (dd, J = 11.5, 6.5 Hz, 1H), 3.09 (dd, J = 12.8, 4.3 Hz, 1H), 2.97-2.59 (m, 6H), 2.22 (ddd, J = 20.1, 10.6, 4.5 Hz, 2H), 2.08 (dd, J = 16.2, 6.3 Hz, 1H), 1.72 (t, J = 10.1 Hz, 1H). |

TABLE I-continued

| Example No | NAME | NMR |
|---|---|---|
| 6 | 1-(((1S,2R)-2-((3,4-dichlorophenoxy)methyl)cyclobutyl)methyl)-4-methylpiperidine | $^1$H NMR (250 MHz, CDCl$_3$) δ 7.33 (d, J = 8.9 Hz, 1H), 7.02 (d, J = 2.8 Hz, 1H), 6.77 (dd, J-8.9, 2.9 Hz, 1H), 4.08 (ddd, J = 41.3, 9.2, 6.5 Hz, 2H), 2.82 (dd, J = 12.2, 9.7 Hz, 4H), 2.58 (dd, J = 12.4, 6.2 Hz, 1H), 2.31 (dd, J = 12.5, 7.2 Hz, 1H), 2.14 (dt, J = 9.5, 5.1 Hz, 2H), 1.99-1.72 (m, 4H), 1.60 (d, J = 12.6 Hz, 2H), 1.29 (m, 4H), 0.91 (d, J = 6.0 Hz, 3H). |
| 7 | 4-methyl-1-(((1S,2R)-2-(((1-methyl-5-(trifluoromethyl)-1H-pyrazol-3-yl)oxy)methyl)cyclobutyl)methyl)piperidine | $^1$H NMR (360 MHz, Acetone-d$_6$) δ 6.22 (d, J = 10.8 Hz, 1H), 4.52-4.37 (m, 1H), 4.30 (dt, J = 10.5, 6.5 Hz, 1H), 3.86 (d, J = 4.2 Hz, 3H), 3.38-3.10 (m, 4H), 3.10-2.66 (m, 5H), 2.33-2.10 (m, 3H), 1.71 (dd, J = 11.5, 4.5 Hz, 2H), 1.67-1.42 (m, 4H), 0.97 (d, J = 5.6 Hz, 3H). |
| 8 | 4-methyl-1-(((1S,2R)-2-(((1-methyl-3-(trifluoromethyl)-1H-pyrazol-5-yl)oxy)methyl)cyclobutyl)methyl)piperidine | $^1$H NMR (250 MHz, CDCl$_3$) δ 5.86 (s, 1H), 4.44-4.20 (m, 2H), 3.73 (s, 3H), 3.09-2.91 (m, 4H), 2.79 (dd, J = 12.9, 4.7 Hz, 2H), 2.52-2.30 (m, 1H), 2.30-2.16 (m, 2H), 2.16-1.93 (m, 2H), 1.77 (t, J = 9.8 Hz, 2H), 1.65-1.50 (m, 3H), 1.28 (s, 3H). |
| 9 | 1-methyl-3-(((1R,2S)-2-(pyrrolidin-1-ylmethyl)cyclobutyl)methoxy)-5-(trifluoromethyl)-1H-pyrazole | $^1$H NMR (360 MHz, CDCl$_3$) δ 5.97 (s, 1H), 4.28 (dd, J = 9.9, 7.2 Hz, 1H), 4.15 (dd, J = 10.0, 6.7 Hz, 1H), 3.80 (s, 3H), 2.79 (m, 2H), 2.71 (dd, J = 12.7, 3.7 Hz, 1H), 2.50 (s br, 5H), 2.10 (m, 2H), 1.95-1.81 (m, 1H), 1.75 (s br, 5H). |
| 10 | 4-(((1S,2R)-2-(((1-methyl-5-(trifluoromethyl)-1H-pyrazol-3-yl)oxy)methyl)cyclobutyl)methyl)morpholine | $^1$H NMR (360 MHz, CDCl$_3$) δ 5.97 (s, 1H), 4.22 (ddd, J = 53.1, 9.9, 6.8 Hz, 2H), 3.81 (s, 3H), 3.73-3.58 (m, 4H), 2.87-2.66 (m, 2H), 2.59 (dd, J = 12.3, 6.2 Hz, 1H), 2.48-2.27 (m, 5H), 2.19-1.98 (m, 2H), 1.92-1.65 (m, 2H). |
| 11 | 1-methyl-5-(((1R,2S)-2-(pyrrolidin-1-ylmethyl)cyclobutyl)methoxy)-3-(trifluoromethyl)-1H-pyrazole | $^1$H NMR (360 MHz, CDCl$_3$) δ 5.74 (s, 1H), 4.24 (dd, J = 9.5, 6.9 Hz, 1H), 4.09 (dd, J = 9.4, 7.0 Hz, 1H), 3.64 (s, 3H), 2.87-2.60 (m, 3H), 2.40 (s br, 5H), 2.17-2.06 (m, 3H), 1.77-1.72 (m, 1H), 1.69 (s br, 4H). |

TABLE I-continued

| STRUCTURE | Example No | NAME | NMR |
|---|---|---|---|
| 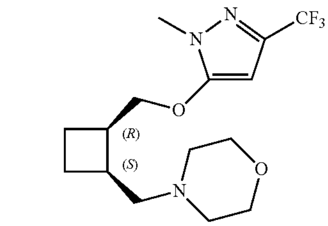 | 12 | 4-(((1S,2R)-2-(((1-methyl-3-(trifluoromethyl)-1H-pyrazol-5-yl)oxy)methyl)cyclobutyl)methyl)morpholine | ¹H NMR (360 MHz, CDCl₃) δ 5.82 (s, 1H), 4.38-4.09 (m, 4H), 3.76-3.60 (m, 5H), 3.38 (d, J = 4.6 Hz, 1H), 3.06 (dd, J = 12.7, 4.3 Hz, 1H), 2.90 (d, J = 11.8 Hz, 3H), 2.79 (dd, J = 12.6, 8.0 Hz, 1H), 2.67 (td, J = 13.6, 3.1 Hz, 2H), 2.31-2.16 (m, 2H), 2.03 (s, 1H), 1.74 (s, 2H). |
| 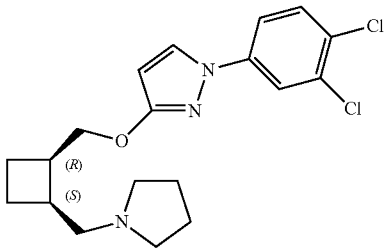 | 13 | 1-(3,4-dichlorophenyl)-3-(((1R,2S)-2-(pyrrolidin-1-ylmethyl)cyclobutyl)methoxy)-1H-pyrazole | ¹H NMR (360 MHz, MeOD-d₄) δ 7.73 (dd, J = 25.4, 2.2 Hz, 2H), 7.52-7.37 (m, 2H), 5.92 (d, J = 2.5 Hz, 1H), 4.37 (ddd, J = 48.0, 10.1, 7.2 Hz, 2H), 2.99-2.70 (m, 3H), 2.65-2.46 (m, 5H), 2.14 (dt, J = 6.5, 4.7 Hz, 2H), 1.93 (t, J = 6.2 Hz, 1H), 1.78 (s, 5H). |
| 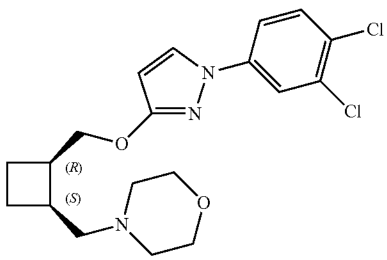 | 14 | 4-(((1S,2R)-2-(((1-(3,4-dichlorophenyl)-1H-pyrazol-3-yl)oxy)methyl)cyclobutyl)methyl)morpholine | ¹H NMR (360 MHz, CDCl₃) δ 8.09 (d, J = 2.7 Hz, 1H), 7.89 (d, J = 2.4 Hz, 1H), 7.59 (dt, J = 20.4, 5.6 Hz, 2H), 5.98 (d, J = 2.6 Hz, 1H), 4.47 (dd, J = 10.3, 7.2 Hz, 1H), 4.31 (dd, J = 10.3, 6.2 Hz, 1H), 3.72-3.59 (m, 4H), 2.93-2.68 (m, 3H), 2.50 (d, J = 2.0 Hz, 4H), 2.25-2.04 (m, 2H), 1.98-1.76 (m, 2H). |
| 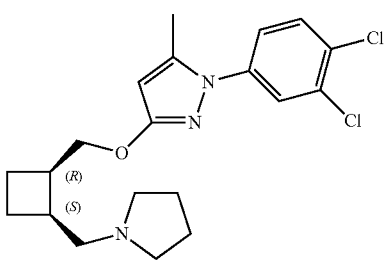 | 15 | 1-(3,4-dichlorophenyl)-5-methyl-3-(((1R,2S)-2-(pyrrolidin-1-ylmethyl)cyclobutyl)methoxy)-1H-pyrazole | ¹H NMR (360 MHz, CDCl₃) δ 7.58 (d, J = 2.4 Hz, 1H), 7.47 (d, J = 8.6 Hz, 1H), 7.28 (dd, J = 8.5, 2.6 Hz, 1H), 5.65 (s, 1H), 4.34 (dd, J = 10.1, 7.3 Hz, 1H), 4.20 (dd, J = 10.1, 7.1 Hz, 1H), 2.88-2.64 (m, 3H), 2.54 (d, J = 9.0 Hz, 1H), 2.47 (s br, 4H), 2.30 (s, 3H), 2.10 (td, J = 7.7, 2.4 Hz, 2H), 1.95-1.81 (m, 1H), 1.73 (s br, 5H). |
| 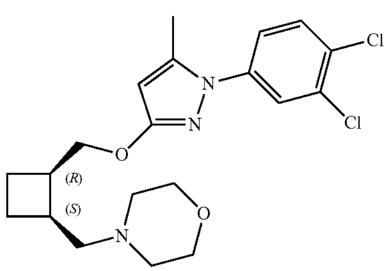 | 16 | 4-(((1S,2R)-2-(((1-(3,4-dichlorophenyl)-5-methyl-1H-pyrazol-3-yl)oxy)methyl)cyclobutyl)methyl)morpholine | ¹H NMR (360 MHz, CDCl₃) δ 7.58 (d, J = 2.2 Hz, 1H), 7.48 (d, J = 8.6 Hz, 1H), 7.28 (dd, J = 9.6, 3.1 Hz, 1H), 5.66 (s, 1H), 4.36 (dd, J = 9.9, 7.3 Hz, 1H), 4.20 (dd, J = 9.9, 6.8 Hz, 1H), 3.67 (s br, 4H), 2.84-2.72 (m, 2H), 2.68-2.55 (m, 1H), 2.40 (s br, 5H), 2.31 (s, 3H), 2.14 (m, 2H), 1.79 (m, 2H). |
| 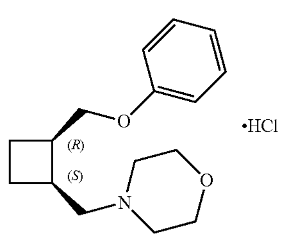 | 17 | 4-(((1S,2R)-2-(phenoxymethyl)cyclobutyl)methyl)morpholine hydrochloride | ¹H NMR (360 MHz, MeOD-d₄) δ 7.30 (dd, J = 8.7, 7.4 Hz, 2H), 7.03-6.90 (m, 3H), 4.35-4.18 (m, 1H), 4.14-3.94 (m, 3H), 3.78 (d, J = 11.9 Hz, 2H), 3.42 (dd, J = 20.6, 15.2 Hz, 4H), 3.22-2.90 (m, 4H), 2.28 (dd, J = 8.3, 5.0 Hz, 2H), 2.21-2.07 (m, 1H), 1.91-1.71 (m, 1H). |

TABLE I-continued

| STRUCTURE | Example No | NAME | NMR |
|---|---|---|---|
| 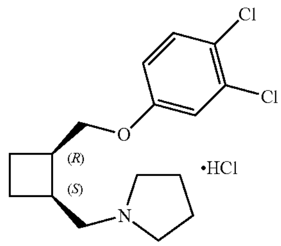 | 18 | 1-(((1S,2R)-2-((3,4-dichlorophenoxy)methyl)cyclobutyl)methyl)pyrrolidine hydrochloride | ¹H NMR (360 MHz, CDCl₃) δ 7.33 (d, J = 8.0 Hz, 1H), 6.97 (s, 1H), 6.74 (d, J = 6.4 Hz, 1H), 4.00 (s, 2H), 3.78 (s, 2H), 2.85 (s, 2H), 2.42 (s, 2H), 2.29 (s, 4H), 2.18 (s, 6H), 1.90 (s, 2H). |
| 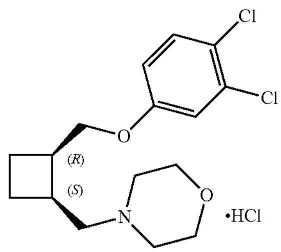 | 19 | 4-(((1S,2R)-2-((3,4-dichlorophenoxy)methyl)cyclobutyl)methyl)morpholine hydrochloride | ¹H NMR (360 MHz, MeOD-d₄) δ 7.39 (d, J = 8.8 Hz, 1H), 7.13 (d, J = 10.4 Hz, 1H), 6.90 (t, J = 7.8 Hz, 1H), 4.37-3.99 (m, 3H), 3.71 (s, 3H), 3.37 (s, 1H), 3.08 (d, J = 12.9 Hz, 1H), 2.93-2.60 (m, 6H), 2.18 (s, 2H), 1.88 (d, J = 55.2 Hz, 1H), 1.73 (s, 1H). |
| 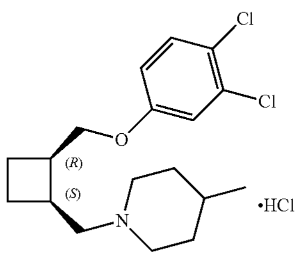 | 20 | 1-(((1S,2R)-2-((3,4-dichlorophenoxy)methyl)cyclobutyl)methyl)-4-methylpiperidine hydrochloride | ¹H NMR (360 MHz, CDCl₃) δ 7.37 (d, J = 8.8 Hz, 1H), 7.03 (d, J = 2.4 Hz, 1H), 6.79 (dd, J = 8.8, 2.4 Hz, 1H), 4.21-3.99 (m, 2H), 3.48 (dd, J = 17.8, 10.9 Hz, 3H), 3.25 (d, J = 12.6 Hz, 1H), 2.98 (s, 2H), 2.59 (dd, J = 26.2, 11.3 Hz, 2H), 2.42-1.90 (m, 7H), 1.79 (d, J = 12.2 Hz, 3H), 1.59 (s, 1H), 1.05 (d, J = 6.4 Hz, 3H). |
| 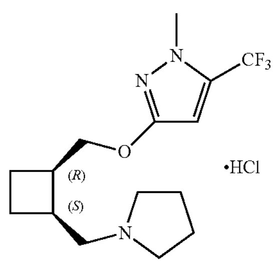 | 21 | 1-methyl-3-(((1R,2S)-2-(pyrrolidin-1-ylmethyl)cyclobutyl)methoxy)-5-(trifluoromethyl)-1H-pyrazole hydrochloride | ¹H NMR (360 MHz, MeOD-d₄) δ 6.24 (s, 1H), 4.37 (dd, J = 10.3, 9.0 Hz, 1H), 4.24 (dd, J = 10.4, 4.8 Hz, 1H), 3.83 (s, 3H), 3.62 (m, 2H), 3.43 (dd, J = 12.8, 5.3 Hz, 1H), 3.35 (d, J = 8.5 Hz, 1H), 3.06 (dd, J = 17.1, 9.0 Hz, 2H), 2.94 (dd, 2H), 2.23 (t, J = 8.2 Hz, 2H), 2.17-1.95 (m, 5H), 1.73 (t, J = 11.7 Hz, 1H). |
| 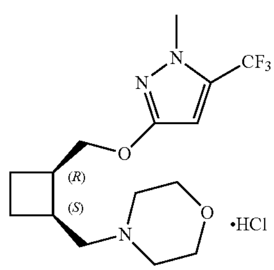 | 22 | 4-(((1S,2R)-2-(((1-methyl-5-(trifluoromethyl)-1H-pyrazol-3-yl)oxy)methyl)cyclobutyl)methyl)morpholine hydrochloride | ¹H NMR (360 MHz, MeOD-d₄) δ 6.25 (s, 1H), 4.32 (ddd, J = 15.6, 10.6, 7.1 Hz, 2H), 4.03 (d, J = 12.8 Hz, 2H), 3.83 (S, 5H), 3.43 (dd, J = 13.1, 5.6 Hz, 3H), 3.15 (t, J = 11.7 Hz, 2H), 3.09-3.00 (m, 1H), 2.97 (dd, J = 7.8, 3.9 Hz, 1H), 2.33-2.19 (m, 2H), 2.19-2.06 (m, 1H), 1.75 (dd, J = 14.2, 6.7 Hz, 1H). |
| 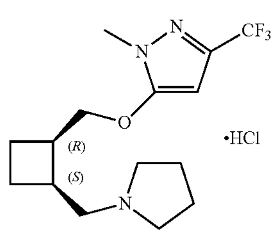 | 23 | 1-methyl-5-(((1R,2S)-2-(pyrrolidin-1-ylmethyl)cyclobutyl)methoxy)-3-(trifluoromethyl)-1H-pyrazole hydrochloride | ¹H NMR (360 MHz, MeOD-d₄) δ 6.12 (s, 1H), 4.47-4.35 (m, 1H), 4.27 (dd, J = 9.5, 5.3 Hz, 1H), 3.92-3.75 (m, 2H), 3.70 (s, 3H), 3.64 (s br, 3H), 3.45 (d, J = 6.4 Hz, 2H), 3.05 (m, 5H), 2.33-1.96 (m, 8H), 1.83 (m, 1H). |

TABLE I-continued

| Example No | NAME | NMR |
|---|---|---|
| 24 | 4-(((1S,2R)-2-(((1-methyl-3-(trifluoromethyl)-1H-pyrazol-5-yl)oxy)methyl)cyclobutyl)methyl)morpholine hydrochloride | $^1$H NMR (360 MHz, MeOD-$d_4$) δ 6.10 (d, J = 8.5 Hz, 1H), 4.39 (dd, J = 32.3, 24.2 Hz, 2H), 4.09-3.91 (m, 2H), 3.80 (dd, J = 11.4, 8.3 Hz, 2H), 3.70 (s, 4H), 3.50-3.41 (m, 3H), 3.25-3.05 (m, 3H), 2.90 (dd, J = 8.1, 3.8 Hz, 2H), 2.37-2.06 (m, 3H), 1.81 (d, J = 38.5 Hz, 1H). |
| 25 | 1-(3,4-dtchlorophenyl)-3-(((1R,2S)-2-(pyrrolidin-1-ylmethyl)cyclobutyl)methoxy)-1H-pyrazole hydrochloride | $^1$H NMR (360 MHz, MeOD-$d_4$) δ 8.15 (d, J = 2.6 Hz, 1H), 7.93 (d, J = 2.3 Hz, 1H), 7.63 (dt, J = 19.3, 5.6 Hz, 2H), 6.07 (d, J = 2.6 Hz, 1H), 4.60-4.27 (m, 2H), 3.65 (s, 2H), 3.57-3.36 (m, 2H), 3.05 (d, J = 33.4 Hz, 4H), 2.40-2.22 (m, 2H), 2.13 (dd, J = 24.7, 18.0 Hz, 5H), 1.82 (d, J = 10.2 Hz, 1H). |
| 26 | 4-(((1S,2R)-2-(((1-(3,4-dichlorophenyl)-1H-pyrazol-3-yl)oxy)methyl)cyclobutyl)methyl)morpholine hydrochloride | $^1$H NMR (360 MHz, MeOD-$d_4$) δ 8.15 (d, J = 2.4 Hz, 1H), 7.91 (d, J = 2.2 Hz, 1H), 7.62 (dt, J = 20.8, 5.5 Hz, 2H), 6.07 (d, J = 2.4 Hz, 1H), 4.55-4.33 (m, 2H), 4.04 (d, J = 13.1 Hz, 2H), 3.85 (dd, J = 20.3, 11.9 Hz, 2H), 3.47 (d, J = 12.6 Hz, 3H), 3.39 (d, J = 8.3 Hz, 1H), 3.24-2.94 (m, 4H), 2.37-2.10 (m, 3H), 1.81 (t, J = 9.9 Hz, 1H). |
| 27 | 1-(3,4-dichlorophenyl)-5-methyl-3-(((1R,2S)-2-(pyrrolidin-1-ylmethyl)cyclobutyl)methoxy)-1H-pyrazole hydrochloride | $^1$H NMR (360 MHz, MeOD-$d_4$) δ 7.71 (d, J = 2.3 Hz, 1H), 7.66 (d, J = 8.7 Hz, 1H), 7.45 (dd, J = 8.6, 2.3 Hz, 1H), 5.90 (s, 1H), 4.47-4.35 (m, 1H), 4.28 (dd, J = 10.5, 5.2 Hz, 1H), 3.74-3.55 (m, 2H), 3.47 (dd, J = 12.7, 5.6 Hz, 1H), 3.41-3.34 (m, 1H), 3.17-2.86 (m, 4H), 2.35 (s, 3H), 2.23 (m, 2H), 2.14 (m, 3H), 2.08-1.96 (m, 2H), 1.77 (m, 1H). |
| 28 | 1-(3,4-dichlorophenyl)-3-(((1R,2R)-2-(pyrrolidin-1-ylmethyl)cyclobutyl)methoxy)-1H-pyrazole | $^1$H NMR (360 MHz, CDCl$_3$) δ 7.75 (d, J = 2.1 Hz, 1H), 7.68 (d, J = 2.5 Hz, 1H), 7.49-7.38 (m, 2H), 5.92 (d, J = 2.5 Hz, 1H), 4.22 (d, J = 3.8 Hz, 2H), 2.73 (d, J = 6.8 Hz, 1H), 2.56-2.36 (m, 7H), 2.18-1.97 (m, 2H), 1.89-1.61 (m, 6H). |

TABLE I-continued

| STRUCTURE | Example No | NAME | NMR |
|---|---|---|---|
| 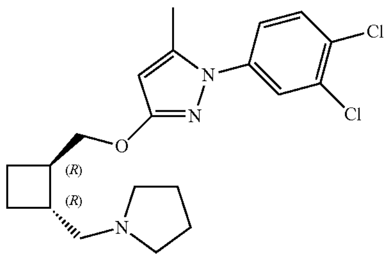 | 29 | 1-(3,4-dichlorophenyl)-5-methyl-3-(((1R,2R)-2-(pyrrolidin-1-ylmethyl)cyclobutyl)methoxy)-1H-pyrazole | ¹H NMR (360 MHz, CDCl₃) δ 7.58 (d, J = 2.5 Hz, 1H), 7.47 (d, J = 8.6 Hz, 1H), 7.28 (dd, J = 8.7, 2.5 Hz, 1H), 5.66 (s, 1H), 4.14 (dd, J = 5.7, 2.2 Hz, 2H), 2.70 (d, J = 8.9 Hz, 1H), 2.48 (s br, 4H), 2.43-2.35 (m, 2H), 2.30 (s, 3H), 2.09 (m, 1H), 2.05-1.92 (m, 1H), 1.75 (s br, 5H), 1.70-1.58 (m, 1H). |
| 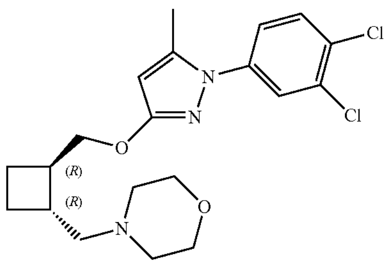 | 30 | 4-(((1R,2R)-2-(((1-(3,4-dichlorophenyl)-5-methyl-1H-pyrazol-3-yl)oxy)methyl)cyclobutyl)methyl)morpholine | ¹H NMR (360 MHz, CDCl₃) δ 7.57 (d, J = 2.4 Hz, 1H), 7.47 (d, J = 8.6 Hz, 1H), 7.31-7.24 (dd, J = 8.6, 2.4 Hz, 1H), 5.65 (s, 1H), 4.13 (d, J = 5.7 Hz, 2H), 3.68 (t, J = 4.6 Hz, 4H), 2.56 (dd, J = 11.2, 4.5 Hz, 1H), 2.49-2.33 (m, 6H), 2.30 (s, 3H), 2.14-1.93 (m, 2H), 1.87-1.72 (m, 1H), 1.72-1.55 (m, 1H). |
| 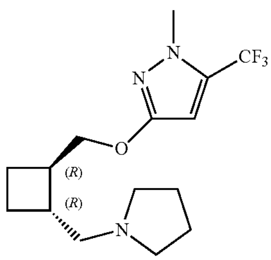 | 31 | 1-methyl-3-(((1R,2R)-2-(pyrrolidin-1-ylmethyl)cyclobutyl)methoxy)-5-(trifluoromethyl)-1H-pyrazole | ¹H NMR (250 MHz, CDCl₃) δ 5.98 (s, 1H), 4.10 (d, J = 7.1 Hz, 2H), 3.81 (s, 3H), 2.99-2.35 (m, 8H), 2.21-1.69 (m, 8H). |
| 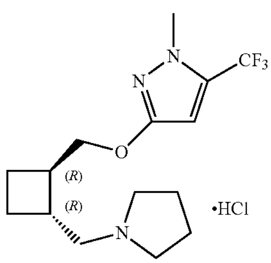 | 32 | 1-methyl-3-(((1R,2R)-2-(pyrrolidin-1-ylmethyl)cyclobutyl)methoxy)-5-(trifluoromethyl)-1H-pyrazole hydrochloride | ¹H NMR (250 MHz, MeOD-d₄) δ 6.20 (s, 1H), 4.15 (qd, J = 10.3, 5.8 Hz, 2H), 3.82 (s, 3H), 3.74-3.55 (m, 2H), 3.50-3.21 (m, 2H), 3.16-2.97 (m, 2H), 2.63 (dt, J = 15.1, 8.3 Hz, 2H), 2.29-1.79 (m, 8H). |
| 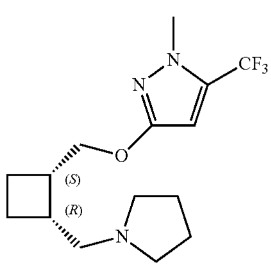 | 33 | 1-methyl-3-(((1S,2R)-2-(pyrrolidin-1-ylmethyl)cyclobutyl)methoxy)-5-(trifluoromethyl)-1H-pyrazole | ¹H NMR (360 MHz, CDCl₃) δ 5.97 (s, 1H), 4.28 (dd, J = 9.9, 7.2 Hz, 1H), 4.15 (dd, J = 10.0, 6.7 Hz, 1H), 3.80 (s, 3H), 2.79 (m, 2H), 2.71 (dd, J = 12.7, 3.7 Hz, 1H), 2.50 (s br, 5H), 2.10 (m, 2H), 1.95-1.81 (m, 1H), 1.75 (s br, 5H). |
| 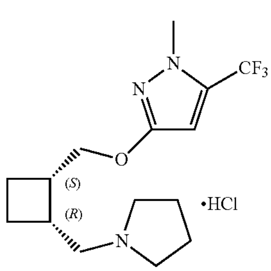 | 34 | 1-methyl-3-(((1S,2R)-2-(pyrrolidin-1-ylmethyl)cyclobutyl)methoxy)-5-(trifluoromethyl)-1H-pyrazole hydrochloride | ¹H NMR (360 MHz, MeOD-d₄) δ 6.24 (s, 1H), 4.37 (dd, J = 10.3, 9.0 Hz, 1H), 4.24 (dd, J = 10.4, 4.8 Hz, 1H), 3.83 (s, 3H), 3.62 (m, 2H), 3.43 (dd, J = 12.8, 5.3 Hz, 1H), 3.35 (d, J = 8.5 Hz, 1H), 3.06 (dd, J = 17.1, 9.0 Hz, 2H), 2.94 (dd, 2H), 2.23 (t, J = 8.2 Hz, 2H), 2.17-1.95 (m, 5H), 1.73 (t, J = 11.7 Hz, 1H). |

TABLE I-continued

| STRUCTURE | Example No | NAME | NMR |
|---|---|---|---|
| 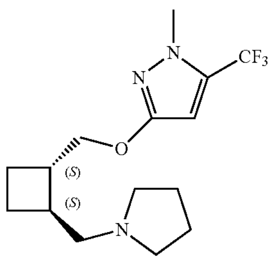 | 35 | 1-methyl-3-(((1S,2S)-2-(pyrrolidin-1-ylmethyl)cyclobutyl)methoxy)-5-(trifluoromethyl)-1H-pyrazole | ¹H NMR (250 MHz, CDCl₃) δ 5.98 (s, 1H), 4.10 (d, J = 7.1 Hz, 2H), 3.81 (s, 3H), 2.99-2.35 (m, 8H), 2.21-1.69 (m, 8H). |
| 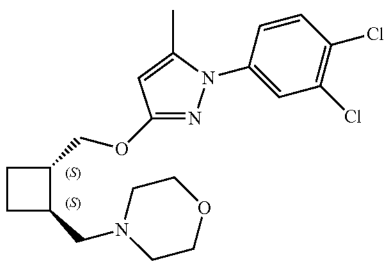 | 36 | 4-(((1S,2S)-2-(((1-(3,4-dichlorophenyl)-5-methyl-1H-pyrazol-3-yl)oxy)methyl)cyclobutyl)methyl)morpholine | ¹H NMR (360 MHz, CDCl₃) δ 7.57 (d, J = 2.4 Hz, 1H), 7.47 (d, J = 8.6 Hz, 1H), 7.31-7.24 (dd, J = 8.6, 2.4 Hz, 1H), 5.65 (s, 1H), 4.13 (d, J = 5.7 Hz, 2H), 3.68 (t, J = 4.6 Hz, 4H), 2.56 (dd, J = 11.2, 4.5 Hz, 1H), 2.49-2.33 (m, 6H), 2.30 (s, 3H), 2.14-1.93 (m, 2H), 1.87-1.72 (m, 1H), 1.72-1.55 (m, 1H). |
| 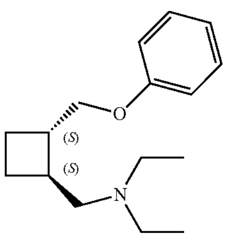 | 37 | N,N-diethyl-N-(((1S,2S)-2-(phenoxymethyl)cyclobutyl)methyl)ethanamine | ¹H NMR (250 MHz, CDCl₃) δ 7.33-7.21 (m, 2H), 6.90 (dd, J = 7.7, 6.6 Hz, 3H), 3.94 (d, J = 3.7 Hz, 2H), 2.71 (dd, J = 11.2, 6.4 Hz, 1H), 2.57 (dd, J = 14.0, 7.0 Hz, 5H), 2.40 (dd, J = 13.6, 6.5 Hz, 2H), 2.20-1.97 (m, 4H), 1.74 (dd, J = 26.2, 10.4 Hz, 2H), 1.04 (d, J = 7.2 Hz, 6H). |
| 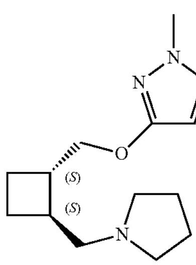 | 38 | 1-methyl-3-(((1S,2S)-2-(pyrrolidin-1-ylmethyl)cyclobutyl)methoxy)-5-(trifluoromethyl)-1H-pyrazole hydrochloride | ¹H NMR (250 MHz, MeOD-d₄) δ 6.20 (s, 1H), 4.15 (qd, J = 10.3, 5.8 Hz, 2H), 3.82 (s, 3H), 3.74-3.55 (m, 2H), 3.50-3.21 (m, 2H), 3.16-2.97 (m, 2H), 2.63 (dt, J = 15.1, 8.3 Hz, 2H), 2.29-1.79 (m, 8H). |
| 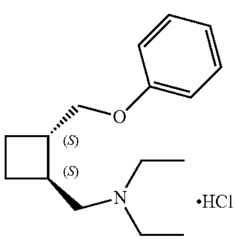 | 39 | N,N-diethyl-N-(((1S,2S)-2-(phenoxymethyl)cyclobutyl)methyl)ethanamine hydrochloride | ¹H NMR (250 MHz, CDCl₃) δ 7.38-7.22 (m, 2H), 6.96 (dd, J = 8.1, 3.2 Hz, 3H), 4.03 (qd, J = 9.6, 5.9 Hz, 2H), 3.43-3.36 (m, 1H), 3.23 (q, J = 7.3 Hz, 5H), 2.78-2.55 (m, 2H), 2.26 (m, 1H), 2.19-2.04 (m, 1H), 1.93 (m, 2H), 1.34 (t, J = 7.3 Hz, 6H). |

BIOLOGICAL ACTIVITY

Pharmacological Study

Human Sigma 1 Receptor Radioligand Assay

To investigate binding properties of sigma 1 receptor ligands to human sigma 1 receptor, transfected HEK-293 membranes and [³H](+)-pentazocine (Perkin Elmer, NET-1056), as the radioligand, were used. The assay was carried out with 7 μg of membrane suspension, 5 nM of [³H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Some of the results obtained are shown in table (II) below:

TABLE II

| Ex | Ki (nM) |
|----|---------|
| 1  | 7.1     |
| 3  | 2.8     |
| 13 | 16.5    |
| 15 | 50.3    |
| 16 | 178.3   |
| 17 | 33.9    |
| 18 | 2.3     |
| 19 | 3.7     |
| 20 | 4.8     |
| 21 | 19.1    |
| 22 | 5.6     |
| 23 | 30.1    |
| 25 | 20.4    |
| 26 | 13.4    |
| 27 | 72.5    |
| 28 | 104.4   |
| 29 | 113.2   |
| 30 | 578.3   |
| 32 | 17.2    |
| 34 | 28.3    |
| 36 | 465.3   |
| 38 | 75.8    |
| 39 | 39.9    |

The invention claimed is:

1. A compound of general formula (I), or a pharmaceutically acceptable salt, isomer, prodrug or solvate thereof:

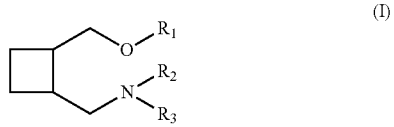

wherein
$R_1$ is selected from the group consisting of substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted arylalkyl, substituted or unsubstituted heteroaryl, substituted or unsubstituted heteroarylalkyl, substituted or unsubstituted non-aromatic heterocyclyl, and substituted or unsubstituted non-aromatic heterocyclylalkyl;
$R_2$ and $R_3$, which may be identical or different, are selected from the group consisting of hydrogen, substituted or unsubstituted alkyl, substituted or unsubstituted cycloalkyl, substituted or unsubstituted cycloalkylalkyl, and substituted or unsubstituted alkenyl;
or
$R_2$ and $R_3$, together with the bridging nitrogen atom to which they are attached, form a substituted or unsubstituted non-aromatic heterocyclyl.

2. The compound according to claim 1, wherein $R_1$ is selected from the group consisting of substituted or unsubstituted aryl and substituted or unsubstituted heteroaryl.

3. The compound according to claim 2, wherein $R_1$ is selected from substituted or unsubstituted $C_6$-$C_{14}$ aryl or substituted or unsubstituted 5- to 10-membered heteroaryl.

4. The compound according to claim 3, wherein $R_1$ is selected from the group consisting of:

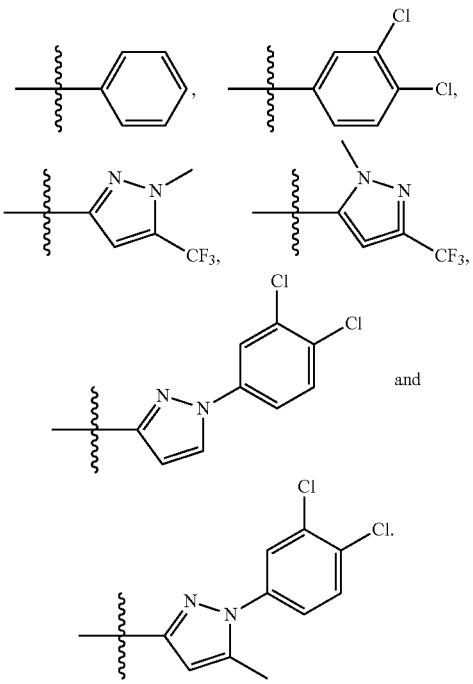

5. The compound according to claim 1, wherein $R_2$ and $R_3$ are independently selected from the group consisting of hydrogen, substituted or unsubstituted alkyl, and substituted or unsubstituted cycloalkyl, or $R_2$ and $R_3$, together with the bridging nitrogen atom to which they are attached, form a substituted or unsubstituted non-aromatic heterocyclyl.

6. The compound according to claim 5, wherein $R_2$ and $R_3$, together with the bridging nitrogen atom to which they are attached, form a substituted or unsubstituted 5- to 10-membered non-aromatic heterocyclyl.

7. The compound according to claim 6, wherein $R_2$ and $R_3$, together with the bridging nitrogen to which they are attached, atom form a non-aromatic heterocyclyl selected from the group consisting of:

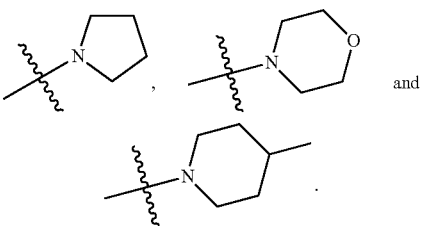

8. The compound according to claim 1, which is selected from:
1-(((1S,2R)-2-(Phenoxymethyl)cyclobutyl)methyl)pyrrolidine,
4-(((1S,2R)-2-(Phenoxymethyl)cyclobutyl)methyl)morpholine,
4-methyl-1-(((1S,2R)-2-(Phenoxymethyl)cyclobutyl)methyl)piperidine,
1-(((1S,2R)-2-((3,4-Dichlorophenoxy)methyl)cyclobutyl)methyl)pyrrolidine,
4-(((1S,2R)-2-((3,4-Dichlorophenoxy)methyl)cyclobutyl)methyl)morpholine, 1-(((1S,2R)-2-((3,4-Dichlorophenoxy)methyl)cyclobutyl)methyl)-4-methylpiperidine,
4-Methyl-1-(((1S,2R)-2-(((1-methyl-5-(trifluoromethyl)-1H-pyrazol-3-yl)oxy)methyl)cyclobutyl)methyl)piperidine,
4-Methyl-1-(((1S,2R)-2-(((1-methyl-3-(trifluoromethyl)-1H-pyrazol-5-yl)oxy)methyl)cyclobutyl)methyl)piperidine,
1-Methyl-3-(((1R,2S)-2-(pyrrolidin-1-ylmethyl)cyclobutyl)methoxy)-5-(trifluoromethyl)-1H-pyrazole,
4-(((1S,2R)-2-(((1-Methyl-5-(trifluoromethyl)-1H-pyrazol-3-yl)oxy)methyl)cyclobutyl)methyl)morpholine,
1-Methyl-5-(((1R,2S)-2-(pyrrolidin-1-ylmethyl)cyclobutyl)methoxy)-3-(trifluoromethyl)-1H-pyrazole,
4-(((1S,2R)-2-(((1-Methyl-3-(trifluoromethyl)-1H-pyrazol-5-yl)oxy)methyl)cyclobutyl)methyl)morpholine,
1-(3,4-Dichlorophenyl)-3-(((1R,2S)-2-(pyrrolidin-1-ylmethyl)cyclobutyl)methoxy)-1H-pyrazole,
4-(((1S,2R)-2-(((1-(3,4-Dichlorophenyl)-1H-pyrazol-3-yl)oxy)methyl)cyclobutyl)methyl)morpholine,
1-(3,4-Dichlorophenyl)-5-methyl-3-(((1R,2S)-2-(pyrrolidin-1-ylmethyl)cyclobutyl)methoxy)-1H-pyrazole,
4-(((1 S,2R)-2-(((1-(3,4-Dichlorophenyl)-5-methyl-1H-pyrazol-3-yl)oxy)methyl)cyclobutyl)methyl)morpholine,
4-(((1S,2R)-2-(Phenoxymethyl)cyclobutyl)methyl)morpholine hydrochloride,
1-(((1S,2R)-2-((3,4-Dichlorophenoxy)methyl)cyclobutyl)methyl)pyrrolidine hydrochloride,
4-(((1S,2R)-2-((3,4-Dichlorophenoxy)methyl)cyclobutyl)methyl)morpholine hydrochloride,
1-(((1 S,2R)-2-((3,4-dichlorophenoxy)methyl)cyclobutyl)methyl)-4-methylpiperidine hydrochloride,
1-Methyl-3-(1R,2S)-2-(pyrrolidin-1-ylmethyl)cyclobutyl)methoxy)-5-(trifluoromethyl)-1H-pyrazole hydrochloride,
4-(1S,2R)-2-(((1-methyl-5-(trifluoromethyl)-1H-pyrazol-3-yl)oxy)methyl)cyclobutyl)methyl)morpholine hydrochloride,
1-Methyl-5-(((1R,2S)-2-(pyrrolidin-1-ylmethyl)cyclobutyl)methoxy)-3-(trifluoromethyl)-1H-pyrazole hydrochloride,
4-(((1S,2R)-2-(((1-Methyl-3-(trifluoromethyl)-1H-pyrazol-5-yl)oxy)methyl)cyclobutyl)methyl)morpholine hydrochloride,
1-(3,4-Dichlorophenyl)-3-(((1R,2S)-2-(pyrrolidin-1-ylmethyl)cyclobutyl)methoxy)-1H pyrazole hydrochloride,
4-(1S,2R)-2-(((1-(3,4-Dichlorophenyl)-1H-pyrazol-3-yl)oxy)methyl)cyclobutyl)methyl)morpholine hydrochloride,
1-(3,4-Dichlorophenyl)-5-methyl-3-(1R,2S)-2-(pyrrolidin-1-ylmethyl)cyclobutyl)methoxy)-1H-pyrazole hydrochloride,
1-(3,4-Dichlorophenyl)-3-(1R,2R)-2-(pyrrolidin-1-ylmethyl)cyclobutyl)methoxy)-1H-pyrazole,
1-(3,4-Dichlorophenyl)-5-methyl-3-(((1R,2R)-2-(pyrrolidin-1-ylmethyl)cyclobutyl)methoxy)-1H-pyrazole,
4-(1R,2R)-2-(((1-(3,4-Dichlorophenyl)-5-methyl-1H-pyrazol-3-yl)oxy)methyl)cyclobutyl)methyl)morpholine,
1-Methyl-3-(((1R,2R)-2-(pyrrolidin-1-ylmethyl)cyclobutyl)methoxy)-5-(trifluoromethyl)-1H-pyrazole,
1-Methyl-3-(((1R,2R)-2-(pyrrolidin-1-ylmethyl)cyclobutyl)methoxy)-5-(trifluoromethyl)-1H-pyrazole hydrochloride,
1-Methyl-3-(((1S,2R)-2-(pyrrolidin-1-ylmethyl)cyclobutyl)methoxy)-5-(trifluoromethyl)-1H-pyrazole,
1-Methyl-3-(((1S,2R)-2-(pyrrolidin-1-ylmethyl)cyclobutyl)methoxy)-5-(trifluoromethyl)-1H-pyrazole hydrochloride,
1-Methyl-3-(((1S,2S)-2-(pyrrolidin-1-ylmethyl)cyclobutyl)methoxy)-5-(trifluoromethyl)-1H-pyrazole,
4-(((1S,2S)-2-(((1-(3,4-Dichlorophenyl)-5-methyl-1H-pyrazol-3-yl)oxy)methyl)cyclobutyl)methyl)morpholine,
N,N-Diethyl-N-(((1S,2S)-2-(phenoxymethyl)cyclobutyl)methyl)ethanamine,
1-methyl-3-(((1S,2S)-2-(pyrrolidin-1-ylmethyl)cyclobutyl)methoxy)-5-(trifluoromethyl)-1H-pyrazole hydrochloride,
N,N-Diethyl-N-(((1S,2S)-2-(phenoxymethyl)cyclobutyl)methyl)ethanamine hydrochloride,
or a solvate or prodrug thereof as well as any pharmaceutically acceptable salt of the free-base compounds.

9. A pharmaceutical composition comprising at least one compound of general formula (I) as defined in claim 1, or a pharmaceutically acceptable salt, isomer, prodrug or solvate thereof, and a pharmaceutically acceptable excipient.

10. A method for the manufacture of a medicament comprising the step of combining a compound of general formula (I) as defined in claim 1 or a pharmaceutically acceptable salt, isomer, prodrug or solvate thereof, with a pharmaceutically acceptable excipient.

11. A method for the treatment of a sigma-1 receptor-mediated disease or condition selected from the group consisting of pain; migraine; arthritis; memory and attention deficits; cognition disorders; neurodegenerative diseases; addiction to drugs and chemical substances; epilepsy; stress; and psychotic conditions, the method comprising administering to the subject in need of such a treatment a therapeutically effective amount of a compound of general formula (I) as defined in claim 1 or a pharmaceutically acceptable salt, isomer, prodrug or solvate thereof.

12. The method according to claim 11, wherein the pain is selected from neuropathic pain, inflammatory pain and other pain conditions involving allodynia and/or hyperalgesia.

13. The method according to claim 11, wherein the addiction to drugs and chemical substances is selected from addiction to cocaine, amphetamine, ethanol and nicotine; and
wherein the psychotic conditions are selected from depression, anxiety and schizophrenia.

* * * * *

UNITED STATES PATENT AND TRADEMARK OFFICE
CERTIFICATE OF CORRECTION

| | | |
|---|---|---|
| PATENT NO. | : 9,464,069 B2 | Page 1 of 1 |
| APPLICATION NO. | : 14/907899 | |
| DATED | : October 11, 2016 | |
| INVENTOR(S) | : Antoni Torrens-Jover et al. | |

It is certified that error appears in the above-identified patent and that said Letters Patent is hereby corrected as shown below:

In the Claims

Column 62, Lines 40 & 41: "nitrogen to which they are attached, atom" should be -- nitrogen atom to which they are attached, --.

Signed and Sealed this
Fifth Day of June, 2018

Andrei Iancu
*Director of the United States Patent and Trademark Office*